(12) United States Patent
O'Connor

(10) Patent No.: US 11,525,152 B2
(45) Date of Patent: Dec. 13, 2022

(54) SYSTEM AND METHOD FOR RAPID DETECTION OF VIABLE MICROORGANISMS IN LIQUID MEDIA

(71) Applicant: Impedx Diagnostics Inc., Kansas City, KS (US)

(72) Inventor: Stephen D O'Connor, Overland Park, KS (US)

(73) Assignee: Acenxion Biosystems, Inc., Kansas City, KS (US)

( * ) Notice: Subject to any disclaimer, the term of this patent is extended or adjusted under 35 U.S.C. 154(b) by 409 days.

(21) Appl. No.: 16/603,473

(22) PCT Filed: Apr. 6, 2018

(86) PCT No.: PCT/IB2018/052417
§ 371 (c)(1),
(2) Date: Oct. 7, 2019

(87) PCT Pub. No.: WO2018/185728
PCT Pub. Date: Oct. 11, 2018

(65) Prior Publication Data
US 2020/0270669 A1 Aug. 27, 2020

Related U.S. Application Data

(60) Provisional application No. 62/482,740, filed on Apr. 7, 2017.

(51) Int. Cl.
*C12Q 1/04* (2006.01)
*G01N 27/02* (2006.01)
(Continued)

(52) U.S. Cl.
CPC .......... *C12Q 1/04* (2013.01); *B01L 3/502715* (2013.01); *C12M 1/3407* (2013.01); *G01N 27/02* (2013.01)

(58) Field of Classification Search
None
See application file for complete search history.

(56) References Cited

U.S. PATENT DOCUMENTS 6,267,858 B1    7/2001  Parce et al.
6,391,558 B1    5/2002  Henkens et al.
(Continued)

OTHER PUBLICATIONS

International Search Report and Written Opinion for International Patent Application No. PCT/IB2018/52417, dated Jul. 9, 2018, 14 pages.
(Continued)

*Primary Examiner* — Matthew D Krcha
(74) *Attorney, Agent, or Firm* — Blake E. Vande Garde; Avek IP, LLC

(57) ABSTRACT

A system and method for rapid detection of viable microorganisms (e.g., pathogens) in liquid media suspensions utilizes at least two electrodes in electrical communication with a suspension (e.g., liquid media possibly containing microorganisms). Electrical response to an electrical pulse in a short initial time window (e.g., no longer than a time required to attain 95% (or another threshold percentage) of a steady state electrical response value after a change in state of the pulse) permits bulk electrical response of the suspension between the electrodes to be determined before electrical response signals are dominated by double layer formation at surfaces of the electrodes. Pulse application and detection of electrical response to a change in state of a pulse may be repeated over time, with changes in such response being useful to detect microorganism proliferation in a bulk suspension.

20 Claims, 27 Drawing Sheets

(51) Int. Cl.
　　　*B01L 3/00*　　　(2006.01)
　　　*C12M 1/34*　　　(2006.01)

(56) References Cited

U.S. PATENT DOCUMENTS

| | | |
|---|---|---|
| 8,635,028 B2 | 1/2014 | Sengupta et al. |
| 2001/0053535 A1 | 12/2001 | Bashir et al. |
| 2005/0048599 A1 | 3/2005 | Goldberg et al. |
| 2005/0112544 A1* | 5/2005 | Xu .................. C12M 41/36<br>435/287.1 |
| 2011/0081676 A1* | 4/2011 | Sengupta ................ C12Q 1/06<br>435/287.1 |
| 2011/0144469 A1 | 6/2011 | Connolly et al. |

OTHER PUBLICATIONS

International Preliminary Report on Patentability for International Patent Application No. PCT/IB2018/52417, dated Oct. 17, 2019, 13 pages.

* cited by examiner

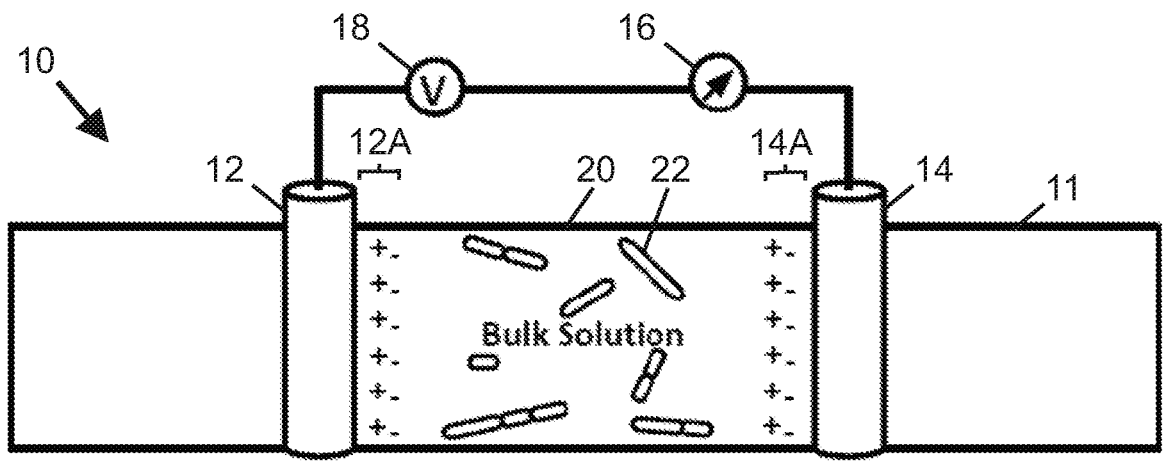
*FIG. 1A*
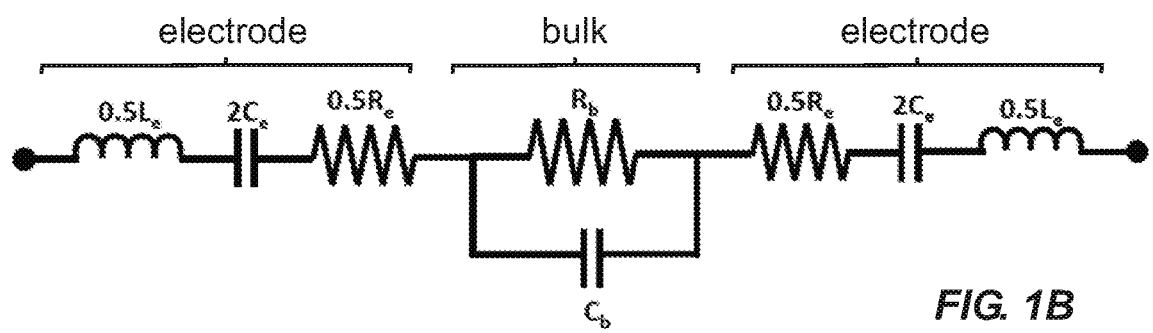
*FIG. 1B*
$$Z_{measured} = \left(R_e + \frac{R_b}{1+\omega^2 R_b^2 C_b^2}\right) - j\left(\frac{1}{\omega C_e} + \frac{\omega R_b^2 C_b}{1+\omega^2 R_b^2 C_b^2}\right)$$
*FIG. 1C*

SYSTEM AND METHOD FOR RAPID DETECTION OF VIABLE MICROORGANISMS IN LIQUID MEDIA

CROSS-REFERENCE TO RELATED APPLICATION(S)

This application is a 35 U.S.C. § 371 national phase filing of International Application No. PCT/IB2018/052417 filed on Apr. 6, 2018 and claims the benefit of U.S. Provisional Patent Application No. 62/482,740 filed on Apr. 7, 2017, wherein the entire disclosures of the foregoing applications are hereby incorporated by reference herein.

TECHNICAL FIELD

The present disclosure relates to systems and methods for detecting presence and/or concentration of microorganisms in liquid media (e.g., suspensions) utilizing electrical signals.

BACKGROUND

Microorganisms or pathogens, such as bacteria, viruses, fungi, yeasts, and molds, can readily proliferate in various media. Contexts in which it may be valuable to rapidly detect the presence of viable microorganisms include infectious disease diagnosis in mammalian fluid samples and treatment as well as quality testing of consumable items such as food, beverages (including water), and pharmaceuticals.

Bloodstream infections (septicemia) and the systemic inflammation they produce (sepsis) represent serious healthcare concerns. Sepsis is most frequently caused by bacterial infections, but it may also be attributable to viral, fungal, or yeast infections. An infection can begin anywhere bacteria or other infectious agents enter the body, such as via an abrasion or wound site, or as a byproduct of a more serious medical problem such as appendicitis, pneumonia, meningitis, or a urinary tract infection. Because sepsis can begin in different parts of the body, it can have different symptoms.

Prompt identification and treatment of the primary cause (or causes) of infection are essential to control of sepsis. When faced with a patient exhibiting symptoms that may suggest sepsis, medical personnel may administer broad-spectrum antibiotics (to kill or reduce proliferation of many types of bacteria, such as both gram-positive and gram-negative varieties), and initiate processes to confirm the existence of a bloodstream infection as well as identify the responsible pathogen. Existence of an infection may be confirmed by culturing and analyzing one or more body fluids (e.g., blood, but possibly also including urine, sputum, etc.), which traditionally has required 12-72 hours to obtain a positive result and up to 120 hours for a result to be deemed negative. For certain pathogenic infections (such as Tuberculosis), the time to obtain a positive result can be even longer. A common treatment regimen involves initial administration of broad-spectrum antibiotics to reduce proliferation of many types of bacteria (e.g., both gram-positive and gram-negative varieties) before culture results and antimicrobial susceptibility are known. For positive cultures, bacteria may be identified by various methods (e.g., biochemical tests or PCR-based DNA analysis, requiring additional time but less than the initial culture step) before targeted antibiotics are administered. For every hour of delay before targeted antibiotic therapy is initiated, the risk of death for a patient afflicted with sepsis may increase significantly (e.g., approximately 7%). Accordingly, reducing the time required to positively determine the presence of a bloodstream infection is expected to significantly reduce mortality attributable to sepsis.

Application of alternating current (AC) electrical signals to liquid suspensions provides a basis for detecting the presence of microorganisms, as disclosed in U.S. Pat. No. 8,635,028 to Sengupta et al. ("the Sengupta patent"). The underlying principle is that in the presence of an AC electric field, a viable (intact) bacterial cell membrane becomes polarized, leading to the buildup of charges across the membrane such that viable microbial cells behave like electrical capacitors. An increase in the number of bacteria due to proliferation results in a corresponding increase in bulk capacitance of the bacteria-containing suspension, due to an increase in the total amount of charge stored by the microorganisms. This increase in total amount of charge cannot be directly measured, however, since the capacitance at each solid-liquid interface (i.e., forming a "double layer") between an electrode and the suspension is dramatically larger (e.g., ~1000 times larger) than the bulk capacitance of the bacteria-containing suspension. The double layer formed on each electrode includes a first layer of surface charge composed of ions attracted to the electrode surface (e.g., due to chemical interactions), and a second layer of ions attracted to the surface charge (e.g., via the coulomb force) and serving to electrically screen the first layer. The second layer is made of free ions that move in the fluid under the influence of electrical attraction and thermal motion, and may be referred to as the "diffuse layer."

FIG. 1A is a schematic diagram of an impedance detection system 10 utilizing a channel 11 containing first and second electrodes 12, 14 arranged to contact a bulk liquid suspension 20 containing microorganisms 22. The electrodes 12, 14 are coupled between a variable power (e.g., current) source 16 configured to generate an alternating current (AC) signal and a voltmeter 18. Upon application of an electrical potential between the electrodes 12, 14, a double layer 12A, 14A is formed at each electrode 12, 14. FIG. 1B provides an equivalent circuit diagram for the electrodes 12, 14 and bulk liquid suspension 20 of FIG. 1A. FIG. 10 provides an equation for determining impedance utilizing the impedance detection system 10 of FIG. 1A. Other electrode configurations are also possible, as are other channel or well configurations.

To address the difficulty of determining capacitance of a bulk liquid suspension in view of its value being screened by capacitance of a double layer, the Sengupta patent discloses the use of an Agilent 4294A Impedance Analyzer instrument to measure the electrical impedance between two electrodes wetted with a bacteria-containing liquid suspension at multiple (>500) frequencies from 1 kHz to 100 MHz. The instrument measured the magnitude and phase of the AC current that flows through the suspension upon the application of a sinusoidal AC voltage that flows through the suspension of 500 mV (peak-to-peak), and calculated the impedance (i.e., resistance and reactance) from the measurements. Since the current is not in-phase with the applied sinusoidal voltage, the impedance (which can be considered as the AC analog of DC resistance) has both an in-phase component called the resistance (R), and an out-of-phase component called the reactance (X). The instrument measured R and X values for each sample, over the frequency range of 1 kHz to 100 MHz, and generated an impedance data set containing the values of R and X for each of the multiple frequencies. By measuring values indicative of impedance at multiple predetermined frequencies (i.e., frequency domain impedance sensing), the value of a parameter in a theoretical circuit model reflecting the amount of capacitive charge stored in the interior bulk of a suspension can be determined—and by repeating this step after predetermined intervals of time to reflect changes in bulk capacitance of a suspension, the presence or absence of viable bacteria in the suspension can be determined.

One drawback of the system and method described by the Sengupta patent is that it involves a significant amount of manual labor (i.e., to draw aliquots from an incubated sample every hour for analysis, taking impedance measurements at multiple frequencies, and analyzing the results offline). Additional limitations of the system and method described by the Sengupta patent relate to analysis speed, cost, and complexity. Even if sample handling steps were automated, gathering data while sweeping over a wide range of frequencies (e.g., at hundreds of frequencies within the range of 1 kHz to 100 MHz) is believed to entail at least about two (2) minutes per sample. Additionally, the (analog) instrumentation required to apply AC signals over a wide range of frequencies and to analyze the resulting signals may be complex and relatively expensive.

The art continues to seek improved systems and methods for rapid detection of viable microorganisms in liquid media.

SUMMARY

A system and method for rapid detection of viable microorganisms (e.g., pathogens) in liquid media suspensions utilizes at least two electrodes in electrical communication (e.g., conductive contact) with a possible suspension (e.g., liquid media possibly containing microorganisms). Electrical response to an electrical pulse in a short initial time window (e.g., no longer than a time required to attain 95% of a steady state electrical response value after a change in state of the electrical pulse, or another time window disclosed herein) permits bulk electrical response of the suspension between the electrodes to be determined before electrical response signals are dominated by double layer formation at surfaces of the electrodes (or at surfaces of walls between electrodes and the suspension, in the case of electrodes arranged in non-contacting relationship with the suspension). Application of a pulse and detection of electrical response to a change in state of the pulse may be repeated over time, with changes in such response being useful to detect microorganism proliferation in a bulk suspension. For example, when first and second electrical pulses are applied at first and second times (e.g., initial and subsequent times) across the electrodes, first and second initial electrical response signals are generated, with each signal being indicative of electrical response in a short initial time window (e.g., no longer than a time required to attain 95% of a steady state electrical response value after a change in state of the corresponding electrical pulse, or another time window disclosed herein). Changes in electrical response between the first time and the second time, which may be measured electronically, may evidence proliferation of one or more pathogens in the liquid media.

In certain embodiments, additional measurements may be taken over more extended time periods and used to detect electrical response of the entire composition of the bulk suspension (including liquid media as well as microorganisms), and this extended electrical response may be used to normalize the above-described initial electrical response signals. Such normalization may be useful to address variations in initial liquid media properties of different bulk suspensions and/or variations in liquid media properties of the same bulk suspension with respect to time. Such variations are potentially attributable to pH, salt concentration, chemical composition, peptide/protein concentration, presence of red and/or white blood cells, and/or other parameters. The presence and differing properties of these other constituents may have an effect on electrical response, and it may be desirable to determine their overall effect on a sample-specific basis. Additionally, system configuration differences may have a significant effect on electrical response. Such system configuration differences include, but are not limited to, electrode size, electrode position/spacing, electrode surface quality, overall channel or chamber dimensions, and/or system fouling over time (such as the binding of cells and/or other analytes to certain areas of the system, etc.). Still further, input signals (e.g., voltage and/or current values, pulse shape, etc.) may affect electrical response.

In one aspect, a method for detecting presence of at least one pathogen in a liquid-containing sample includes: applying a first electrical pulse between at least two electrodes in electrical communication with at least a portion of the liquid-containing sample; detecting a first initial electrical response of the at least a portion of the liquid-containing sample and the at least two electrodes due to application of the first electrical pulse, to generate at least one first initial electrical response signal that is indicative of an electrical response in a first initial time window that extends no longer than a time required to attain 95% (or another threshold percentage disclosed herein) of a steady state electrical response value after a change in state of the first electrical pulse; applying a second electrical pulse between the at least two electrodes in electrical communication with at least a portion of the liquid-containing sample; detecting a second initial electrical response of the at least a portion of the liquid-containing sample and the at least two electrodes due to application of the second electrical pulse, to generate at least one second initial electrical response signal that is indicative of an electrical response in a second initial time window that extends no longer than the time required to attain 95% (or another threshold percentage disclosed herein) of the steady state electrical response value after a change in state of the second electrical pulse; and comparing a second electrical response embodying or derived from the at least one second initial electrical response signal to a first electrical response embodying or derived from the at least one first initial electrical response signal. In certain embodiments, the first electrical response may be embodied in or derived solely from the at least one first initial electrical response signal, and the second electrical response may be embodied in or derived solely from the at least one second initial electrical response signal. In other embodiments, further signals may be employed in the derivation of the first and second electrical responses.

In certain embodiments, the at least a portion of the liquid-containing sample to which the first electrical pulse is applied comprises a first portion of the liquid-containing sample; the at least a portion of the liquid-containing sample for which the first initial electrical response is detected comprises the first portion of the liquid-containing sample; the at least a portion of the liquid-containing sample to which the second electrical pulse is applied comprises a second portion of the liquid-containing sample; and the at least a portion of the liquid-containing sample for which the second initial electrical response is detected comprises the second portion of the liquid-containing sample.

In certain embodiments, the at least a portion of the liquid-containing sample to which the first electrical pulse is applied comprises the same at least a portion of the liquid-containing sample to which the second electrical pulse is applied.

In certain embodiments, the at least two electrodes are in electrical communication with a fluidic channel, and the method further comprises: supplying the first portion of the liquid-containing sample to the fluidic channel prior to applying the first electrical pulse; and supplying the second portion of the liquid-containing sample to the fluidic channel prior to applying the second electrical pulse.

In certain embodiments, the method comprises at least one of the following features (i) or (ii): (i) the change in state of the first electrical pulse comprises a current rise or a voltage rise (e.g., corresponding to application of a pulse), or (ii) the change in state of the second electrical pulse comprises a current rise or a voltage rise (e.g., corresponding to application of a pulse).

In certain embodiments, the method comprises at least one of the following features (i) or (ii): (i) the change in state of the first electrical pulse comprises a current drop or a voltage drop (e.g., corresponding to termination of a pulse), or (ii) the change in state of the second electrical pulse comprises a current drop or a voltage drop (e.g., corresponding to termination of a pulse).

In certain embodiments, the at least one first initial electrical response signal comprises a time value corresponding to attainment of a predetermined or user-determined voltage or current value. In certain embodiments, the predetermined or user-determined voltage or current value comprises a defined percentage of the steady state electrical response value.

In certain embodiments, the at least one first initial electrical response signal comprises at least one curve fitting parameter derived from a plurality of measured electrical response values obtained in the first initial time window.

In certain embodiments, each of the first electrical pulse and the second electrical pulse comprises a direct current electrical signal. This direct current electrical signal may be monitored with respect to time.

In certain embodiments, the method further comprises detecting a first extended electrical response of the first portion of the liquid-containing sample and the at least two electrodes due to application of the first electrical pulse, to generate at least one first extended electrical response signal that is indicative of an electrical response in a first extended time window that extends longer than the first initial time window by a factor of at least about 5 (but in certain embodiments is no longer than about 20 microseconds) after the change in state of the first electrical pulse; detecting a second extended electrical response of the second portion of the liquid-containing sample and the at least two electrodes due to application of the second electrical pulse, to generate at least one second extended electrical response signal that is indicative of an electrical response in a second extended time window that extends longer than the second initial time window by a factor of at least about 5 (but in certain embodiments is no longer than about 20 microseconds) after the change in state of the second electrical pulse; and utilizing the at least one first extended electrical response signal to normalize the at least one first initial electrical response signal to derive the first electrical response, and utilizing the at least one second extended electrical response signal to normalize the at least one second initial electrical response signal to derive the second electrical response. Thus, in certain embodiments, the first electrical response may be derived from the at least one first initial electrical response signal in combination with the at least one first extended electrical response signal, and the second electrical response may be derived from the at least one second initial electrical response signal in combination with the at least one second extended electrical response signal. In certain embodiments, the first and second extended time windows extend no longer than a time required to attain 99.8% of the steady state electrical response value. Other time frames longer or shorter than 20 microseconds to define the first and second extended time windows can also be utilized.

In certain embodiments, the first initial time window extends no longer than a time required to attain 90% of the steady state electrical response value after the change in state of the first electrical pulse, and the second initial time window extends no longer than the time required to attain 90% of the steady state electrical response value after the change in state of the second electrical pulse.

In certain embodiments, the first initial time window extends no longer than about 100 nanoseconds after the change in state of the first electrical pulse, and the second initial time window extends no longer than about 100 nanoseconds after the change in state of the second electrical pulse.

In certain embodiments, the method further comprises maintaining the liquid-containing sample in a reservoir under conditions conducive to growth of the at least one pathogen between a time of application of the first electrical pulse and a time of application of the second electrical pulse; wherein the supplying of the first portion of the liquid-containing sample to the fluidic channel comprises transferring the first portion of the liquid-containing sample from the reservoir to the fluidic channel; and wherein the supplying of the second portion of the liquid-containing sample to the fluidic channel comprises transferring the second portion of the liquid-containing sample from the reservoir to the fluidic channel.

In certain embodiments, the method further comprises at least one of the following steps (A) or (B): (A) returning the first portion of the liquid-containing sample from the fluidic channel to the reservoir; or (B) returning the second portion of the liquid-containing sample from the fluidic channel to the reservoir.

In certain embodiments, the second portion of the liquid-containing sample includes at least a subset of the first portion of the liquid-containing sample.

In certain embodiments, the at least two electrodes comprise a first pair of electrodes and a second pair of electrodes; the applying of the first electrical pulse between the at least two electrodes comprises applying the first electrical pulse between the first pair of electrodes; the applying of the second electrical pulse between the at least two electrodes comprises applying the second electrical pulse between the first pair of electrodes; the detecting of the first initial electrical response comprises use of the second pair of electrodes; and the detecting of the second initial electrical response comprises use of the second pair of electrodes.

In certain embodiments, the fluidic channel comprises at least one dimension of less than about 1 mm.

In certain embodiments, the second portion of the liquid-containing sample is supplied to the fluidic channel more than about 10 minutes after the first portion of the liquid-containing sample is supplied to the fluidic channel.

In certain embodiments, the second portion of the liquid-containing sample is supplied to the fluidic channel more than about 1 hour after the first portion of the liquid-containing sample is supplied to the fluidic channel.

In another aspect, a system for detecting presence of at least one pathogen in a liquid-containing sample comprises:

a fluidic channel configured to receive the liquid-containing sample; at least two electrodes in electrical communication with the fluidic channel; pulse generator circuitry operatively coupled with the at least two electrodes to generate a first electrical pulse across the at least two electrodes when the at least two electrodes are in electrical communication with at least a portion of the liquid-containing sample, and to generate a second electrical pulse across the at least two electrodes when the at least two electrodes are in electrical communication with at least a portion of the liquid-containing sample; signal detection circuitry operatively coupled with the at least two electrodes, wherein the signal detection circuitry is configured (i) to detect a first initial electrical response of the at least a portion of the liquid-containing sample due to application of the first electrical pulse to generate at least one first initial electrical response signal indicative of electrical response in a first initial time window extending no longer than a time required to attain 95% (or another threshold percentage disclosed herein) of a steady state electrical response value after a change in state of the first electrical pulse, and (ii) to detect a second initial electrical response of the at least a portion of the liquid-containing sample due to application of the second electrical pulse to generate at least one second initial electrical response signal indicative of electrical response in a second initial time window extending no longer than the time required to attain 95% (or another threshold percentage disclosed herein) of the steady state electrical response value after a change in state of the second electrical pulse; and comparison circuitry operatively coupled with the signal detection circuitry and configured to compare a second electrical response embodying or derived from the at least one second initial electrical response signal to a first electrical response embodying or derived from the at least one first initial electrical response signal.

In certain embodiments, the at least a portion of the liquid-containing sample for which the first electrical pulse is generated comprises a first portion of the liquid-containing sample; the at least a portion of the liquid-containing sample for which the at least one first initial electrical response signal is generated comprises the first portion of the liquid-containing sample; the at least a portion of the liquid-containing sample for which the second electrical pulse is generated comprises a second portion of the liquid-containing sample; and the at least a portion of the liquid-containing sample for which the at least one second initial electrical response signal is generated comprises the second portion of the liquid-containing sample.

In certain embodiments, the system further comprises a reservoir configured to hold the liquid-containing sample, wherein the fluidic channel is configured to receive the first portion of the liquid-containing sample and the second portion of the liquid-containing sample from the reservoir.

In certain embodiments, the system further comprises a fluid transfer device configured to transfer the first portion and the second portion of the liquid-containing sample from the reservoir to the fluidic channel.

In certain embodiments, the at least one first initial electrical response signal comprises a time value corresponding to attainment of a predetermined or user-determined voltage or current value.

In certain embodiments, the at least one first initial electrical response signal comprises at least one curve fitting parameter derived from a plurality of measured electrical response values obtained in the first initial time window.

In certain embodiments, the at least two electrodes comprise a first pair of electrodes and a second pair of electrodes; the pulse generator circuitry is operatively coupled with the first pair of electrodes to generate the first electrical pulse across the first pair of electrodes when the first pair of electrodes is in electrical communication with the at least a portion of the liquid-containing sample; and the signal detection circuitry is operatively coupled with the second pair of electrodes.

In certain embodiments, the fluidic channel comprises at least one dimension of less than about 1 mm.

In another aspect, a method for detecting presence of at least one pathogen in a liquid-containing sample includes: supplying at least a first portion of the liquid-containing sample to a fluidic channel to cause the at least a first portion of the liquid-containing sample to contact at least two electrodes in electrical communication with the fluidic channel; applying a first electrical pulse between the at least two electrodes; detecting a first initial electrical response of the at least a first portion of the liquid-containing sample due to application of the first electrical pulse, to generate at least one first initial electrical response signal that is indicative of electrical response in a first initial time window that extends no longer than a time required to attain 95% (or another threshold percentage disclosed herein) of a steady state electrical response value after a change in state of the first electrical pulse; supplying at least a second portion of the liquid-containing sample to the fluidic channel to cause the at least a second portion of the liquid-containing sample to contact the at least two electrodes; applying a second electrical pulse between the at least two electrodes; detecting a second initial electrical response of the at least a second portion of the liquid-containing sample due to application of the second electrical pulse, to generate at least one second initial electrical response signal that is indicative of electrical response in a second initial time window that extends no longer than the time required to attain 95% (or another threshold percentage disclosed herein) of the steady state electrical response value after a change in state of the second electrical pulse; and comparing a second electrical response embodying or derived from the at least one second initial electrical response signal to a first electrical response embodying or derived from the at least one first initial electrical response signal.

In another aspect, any aspects, embodiments, and/or features disclosed herein may be combined for additional advantage unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

FIG. 1A is a schematic diagram of an impedance detection system utilizing a variable power source and electrodes arranged to contact a bulk liquid suspension containing microorganisms.

FIG. 1B is an equivalent circuit diagram for the electrodes and bulk liquid suspension of FIG. 1A.

FIG. 1C provides an equation for determining impedance utilizing the impedance detection system of FIG. 1A.

averaged rising edge output signals of five 1V DC pulses obtained using a time domain impedance detection (TDID) system according to one embodiment.

Figure 3A:
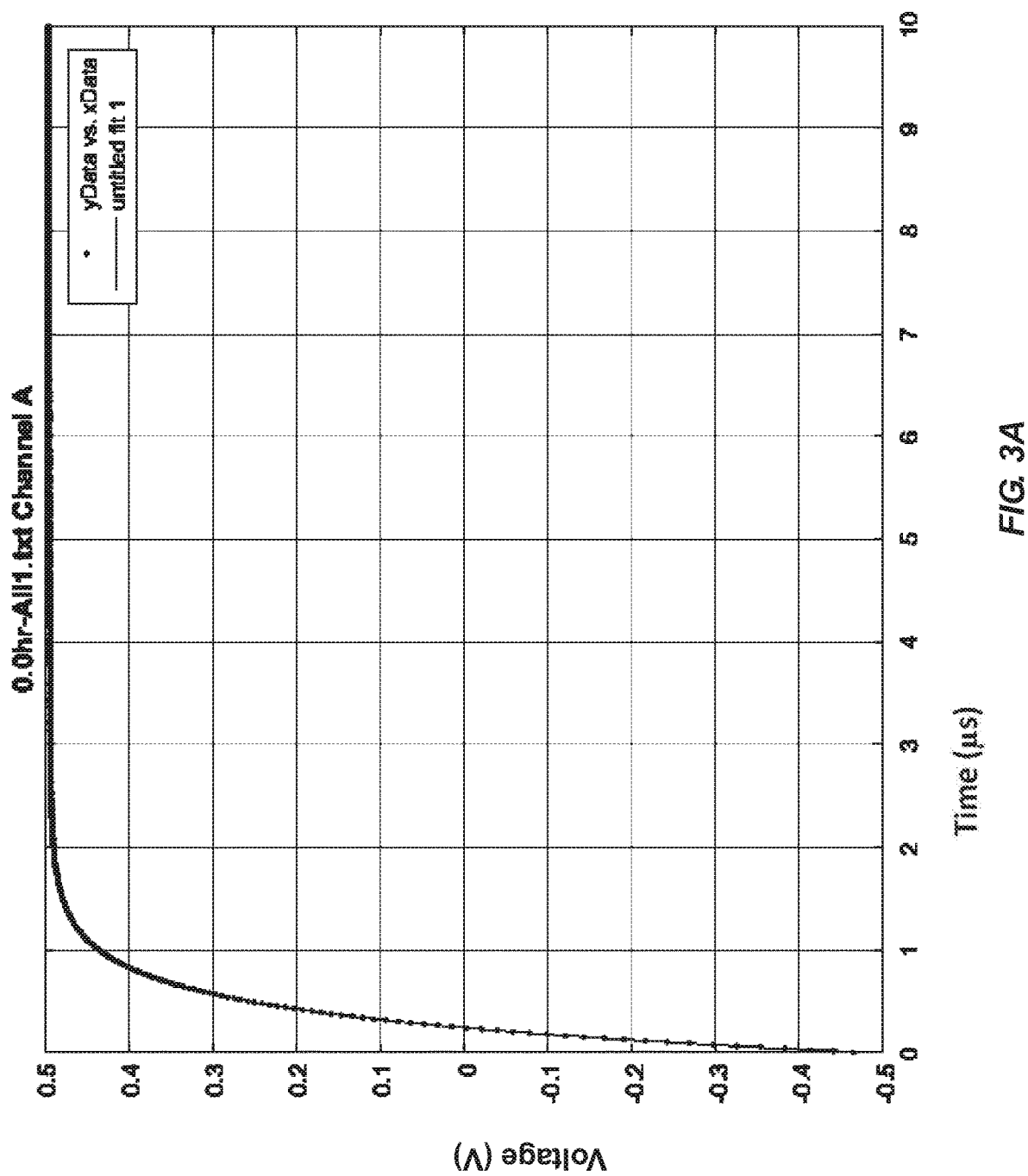

FIG. 3A provides superimposed plots of voltage versus time for a rising edge of a 1V DC pulse output by a TDID system according to one embodiment, including (i) raw output voltage (points) and (ii) curve-fitted output voltage (solid line), over a 10 µs timeframe.

Figure 3B:
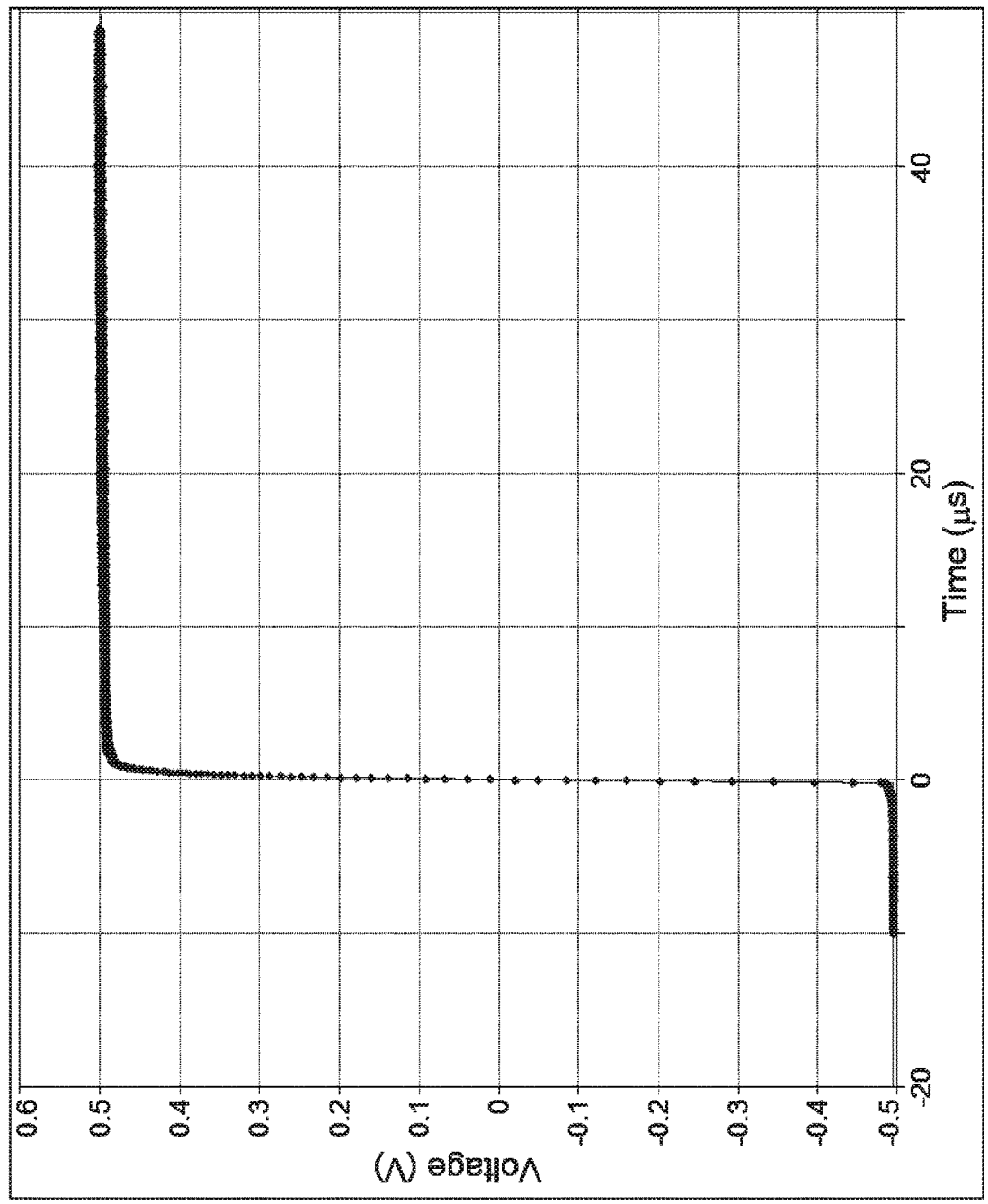

FIG. 3B provides superimposed plots of voltage versus time for a rising edge of the same 1V DC pulse output as FIG. 3A, including (i) raw output voltage (points) and (ii) curve-fitted output voltage (solid line), over a 50 µs timeframe.

Figure 4:
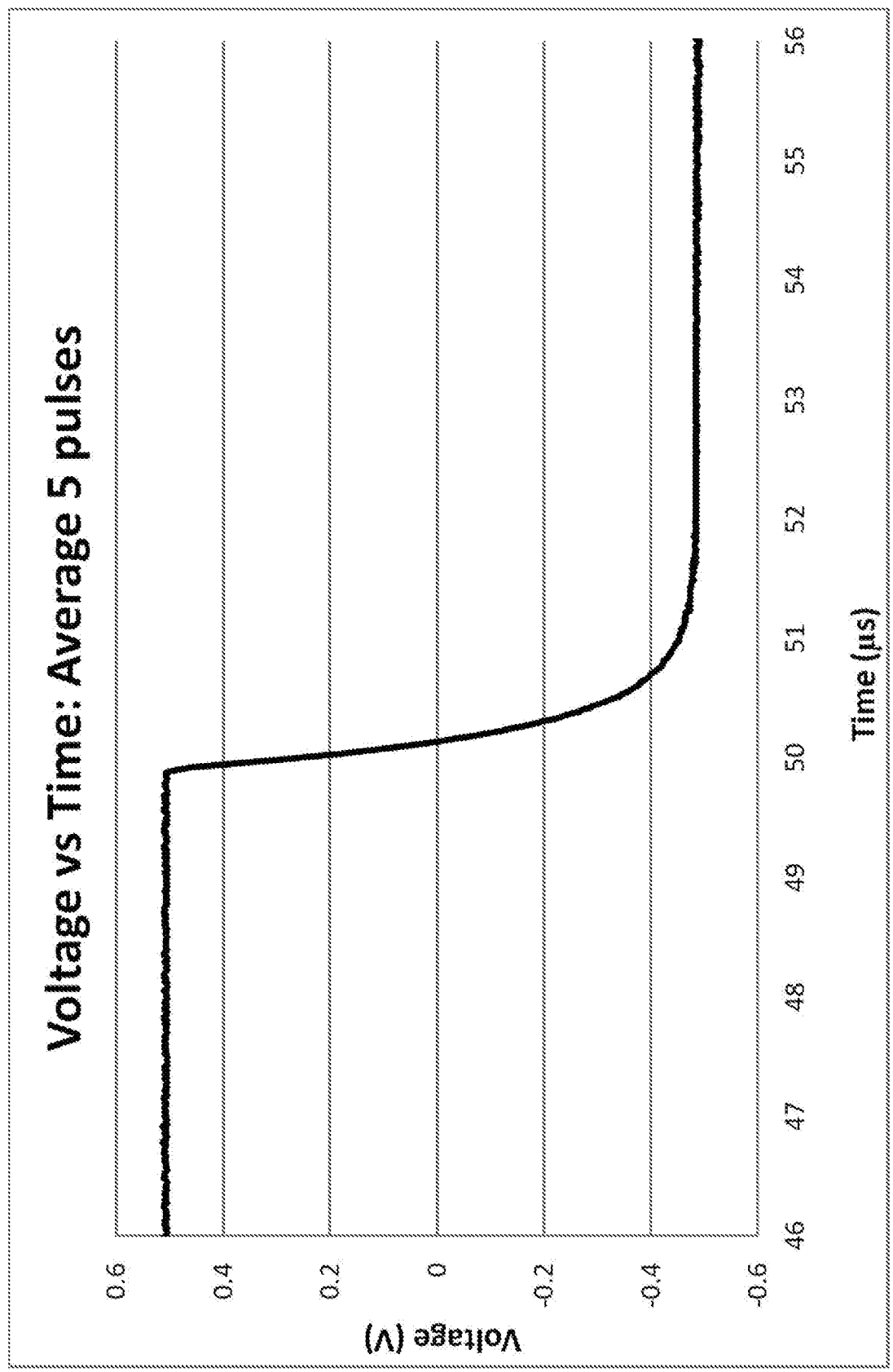

FIG. 4 is a plot of average voltage versus time for falling edges of five 1V DC pulses obtained using a TDID system according to one embodiment.

Figure 5A:
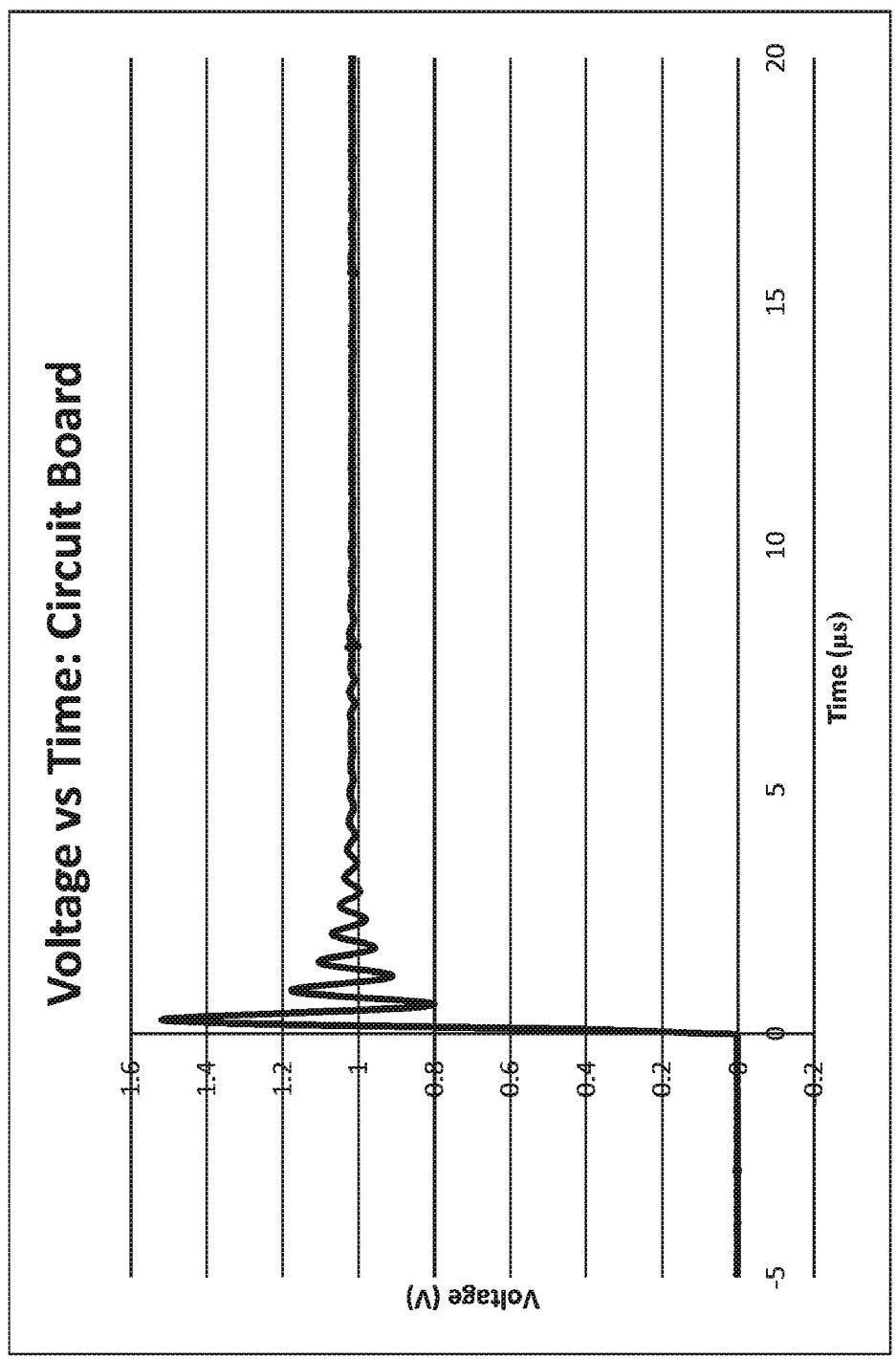

FIG. 5A is a plot of voltage versus time generated by a circuit board for a rising edge of a 1V DC pulse, which exhibits ringing for several seconds.

Figure 5B:
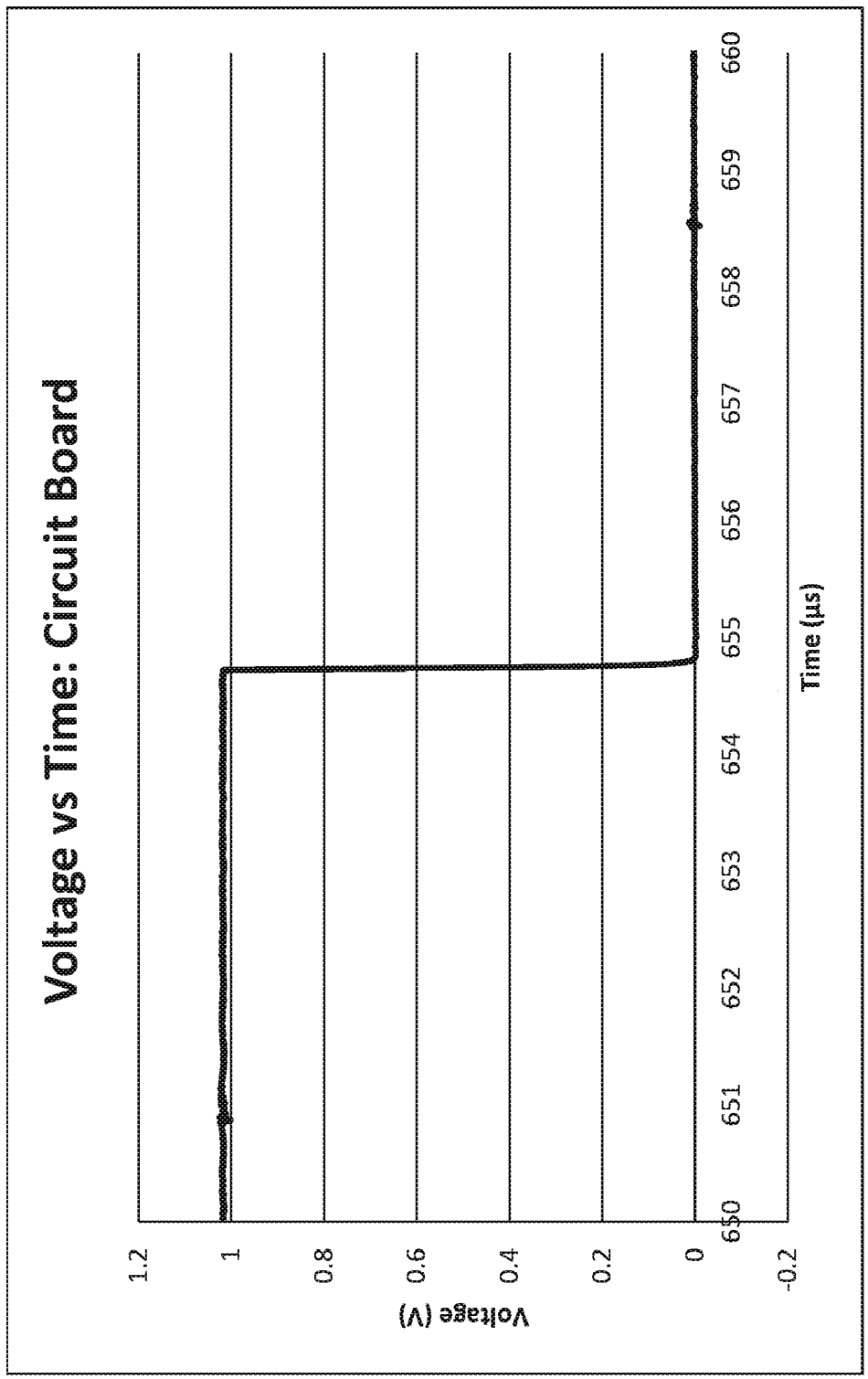

FIG. 5B is a plot of voltage versus time generated by a circuit board for a trailing edge of a 1V DC pulse, with the trailing edge being free from ringing.

Figure 6:
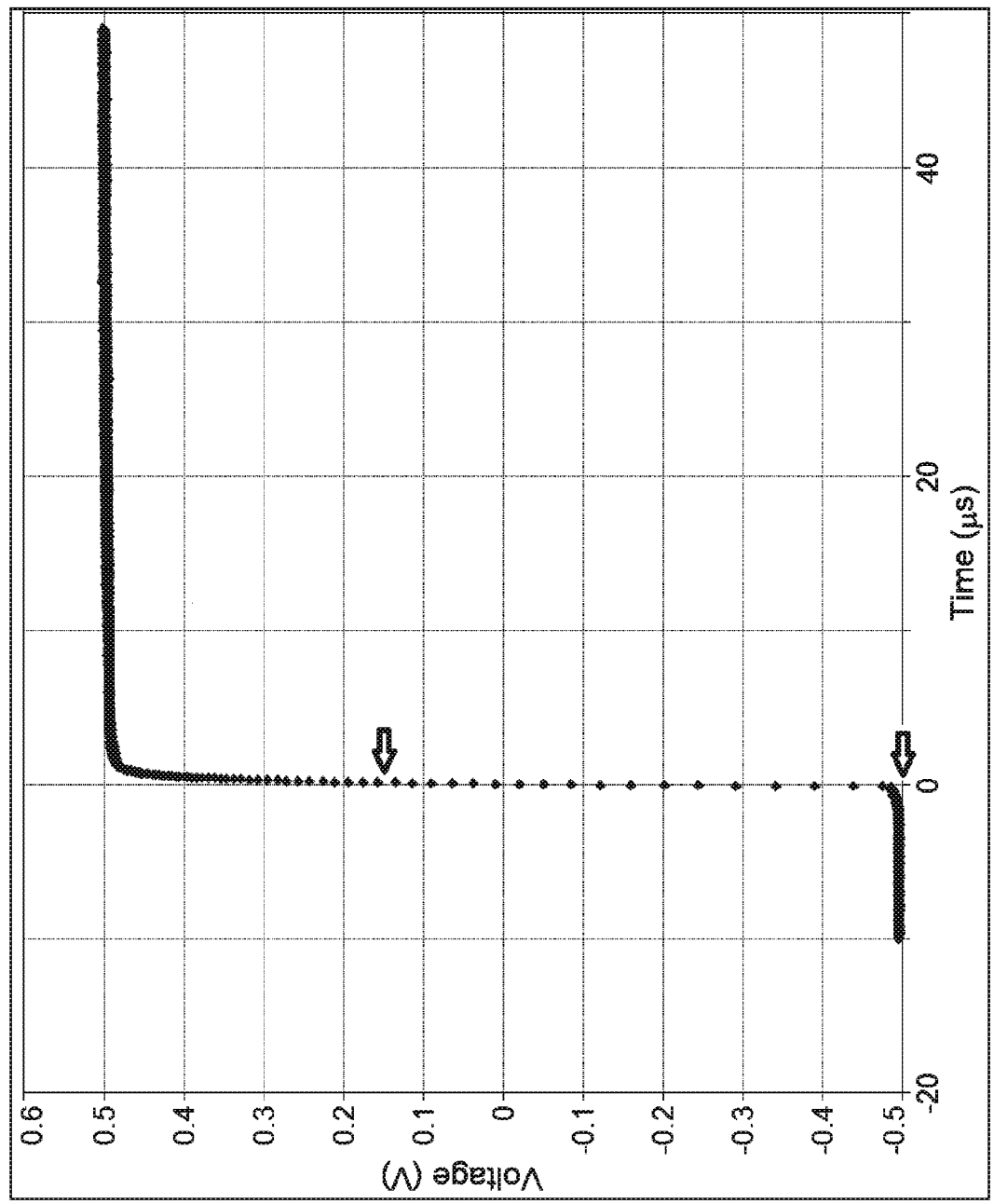

FIG. 6 is a plot of voltage versus time for a rising edge of the same 1V DC pulse output as FIG. 3B (without curvefit), modified to include a first (lower) horizontal arrow corresponding to an initial "base" voltage (−0.5V) and a second (upper) horizontal arrow corresponding to a 66% increase in output voltage, for which the corresponding difference in time may be calculated to determine the rise time, according to one embodiment.

Figure 7:
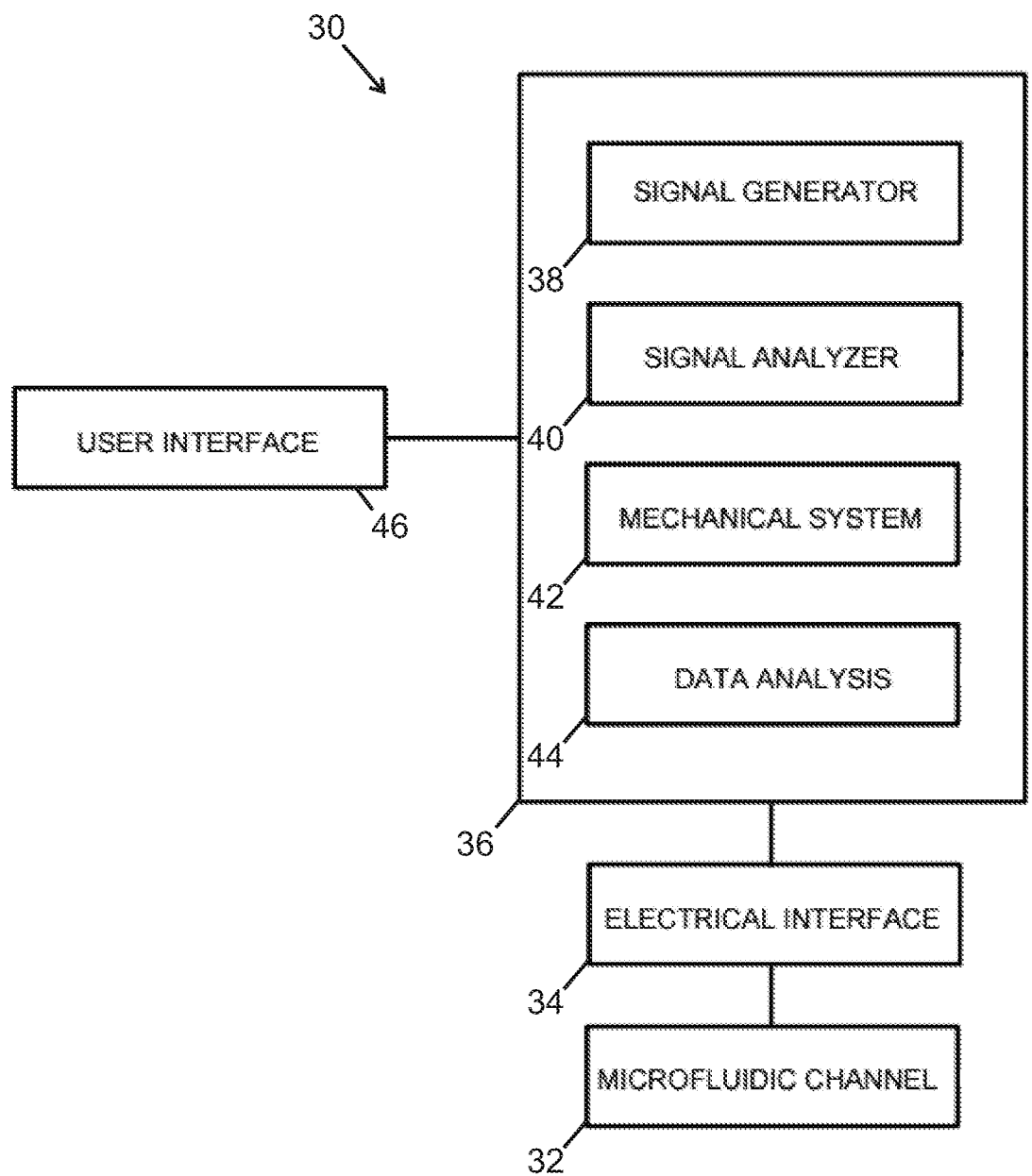

FIG. 7 is a block diagram of components of a time domain impedance detection (TDID) system according to one embodiment of the present disclosure.

Figure 8A:
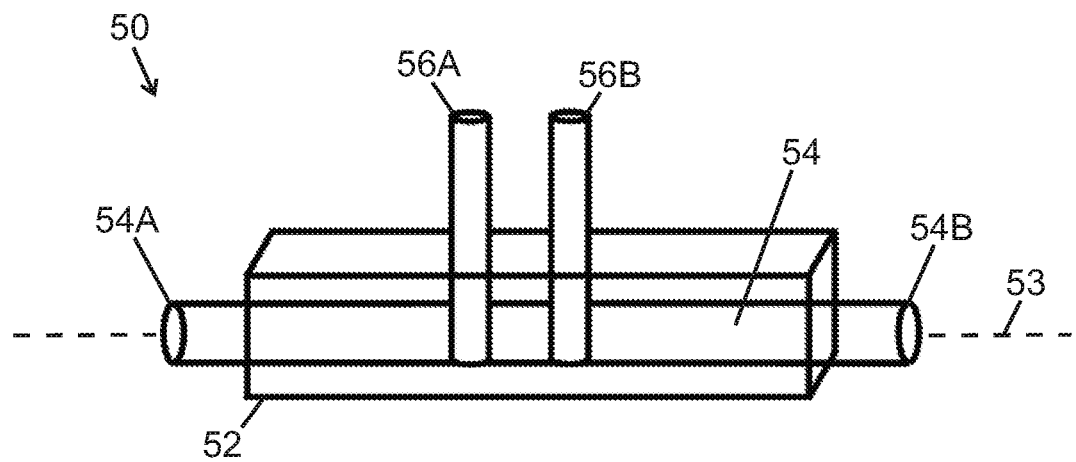

FIG. 8A is a schematic perspective view of a fluidic device including a fluidic channel with extensions protruding through sidewalls of the fluidic device and including two cylindrical electrodes arranged perpendicular to the fluidic channel, with a centerline of each electrode intersecting a centerline of the fluidic channel, according to one embodiment.

Figure 8B:
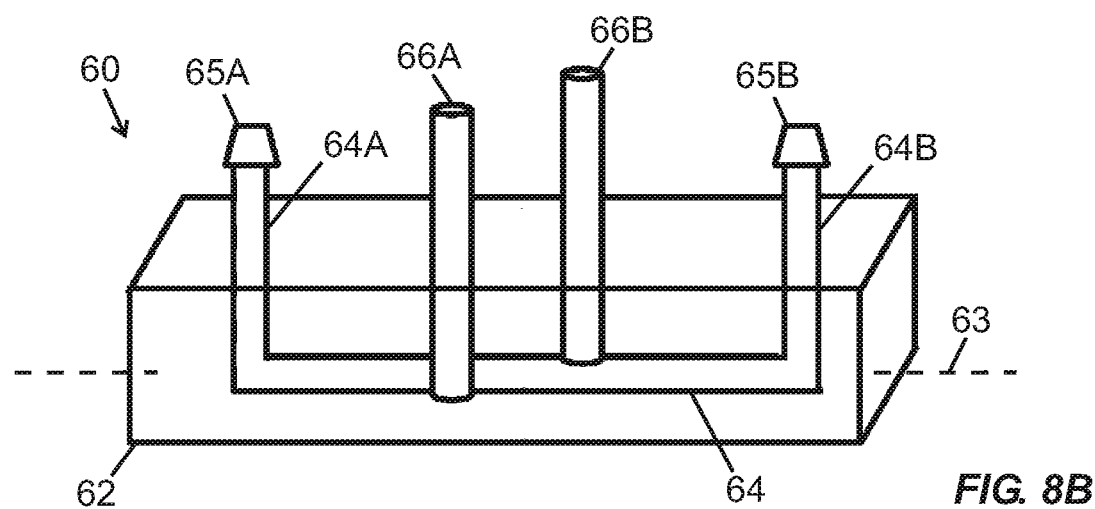

FIG. 8B is a schematic perspective view of a fluidic device including a fluidic channel with extensions protruding through a top wall of the fluidic device, and including two cylindrical electrodes arranged perpendicular to the fluidic channel, with each electrode being offset relative to a centerline of the fluidic channel, according to one embodiment.

Figure 8C:
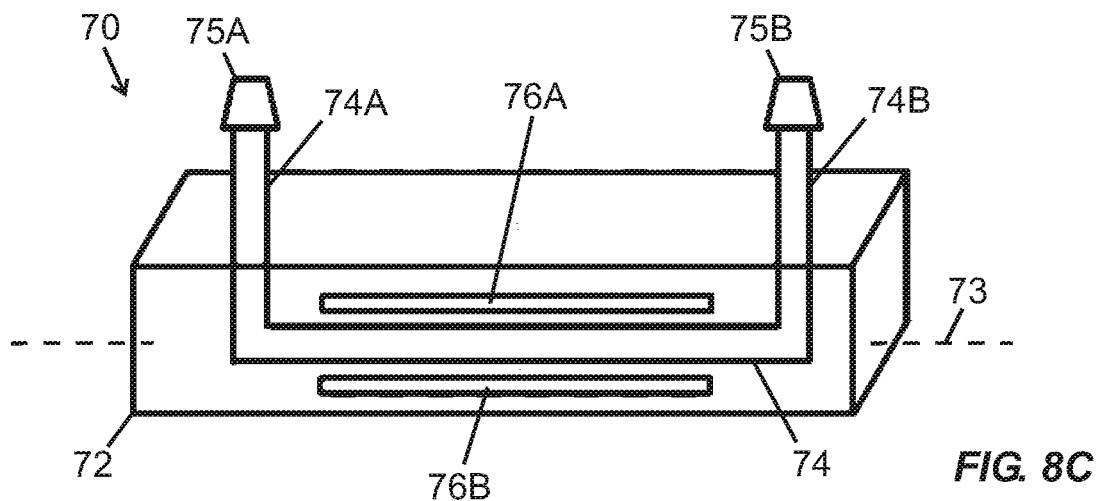

FIG. 8C is a schematic perspective view of a fluidic device including a fluidic channel with extensions protruding through a top wall of the fluidic device, and including two plate-type electrodes arranged along a central portion of the fluidic channel, with one electrode arranged above and another electrode arranged below the fluidic channel, optionally in non-contacting relationship with the fluidic channel, according to one embodiment.

Figure 8D:
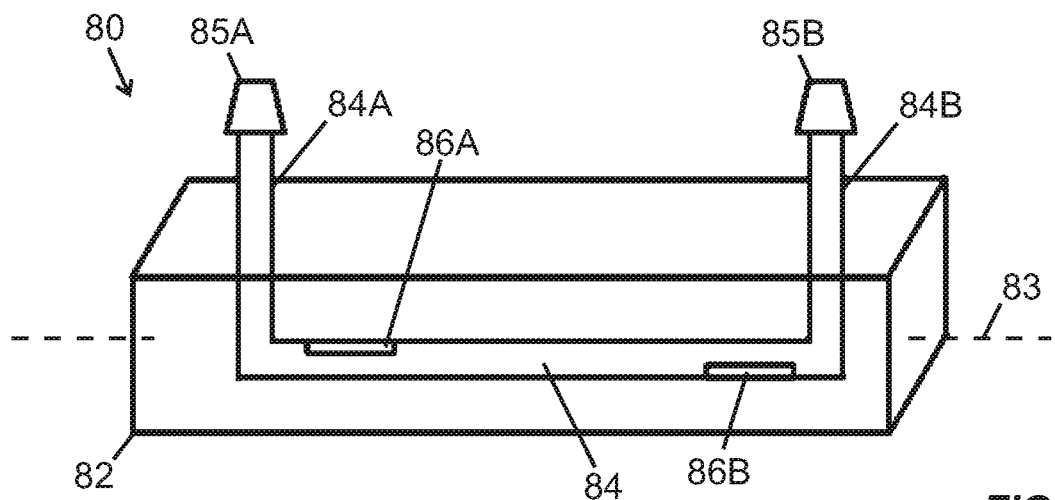

FIG. 8D is a schematic perspective view of a fluidic device including a fluidic channel with extensions protruding through a top wall of the fluidic device, including a first electrode arranged along an upper left boundary of the fluidic channel, and including a second electrode arranged along a lower right boundary of the fluidic channel, according to one embodiment.

Figure 8E:
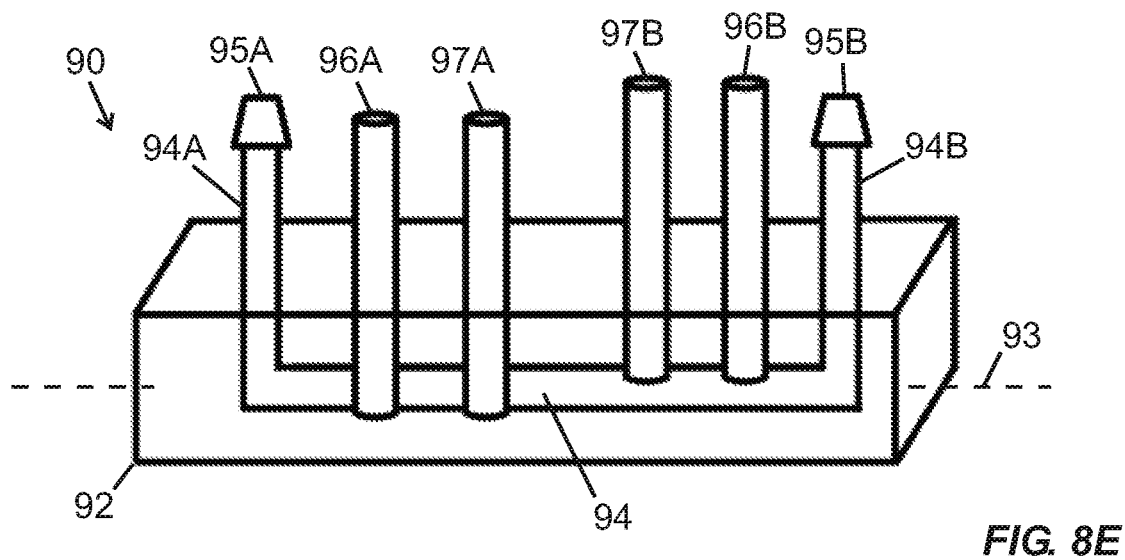

FIG. 8E is a schematic perspective view of a fluidic device including a fluidic channel with extensions protruding through a top wall of the fluidic device, and including two pairs of cylindrical electrodes arranged perpendicular to the fluidic channel, with each electrode being offset relative to a centerline of the fluidic channel, according to one embodiment.

Figure 9A:
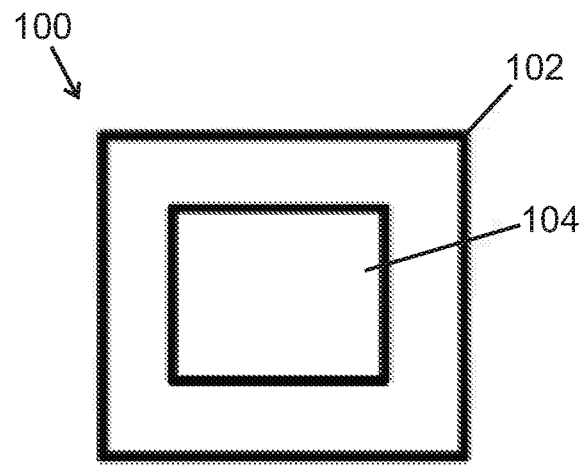

FIG. 9A is a schematic cross-sectional view of a portion of a fluidic device including a fluidic channel having a square-like cross-sectional shape, according to one embodiment.

Figure 9B:
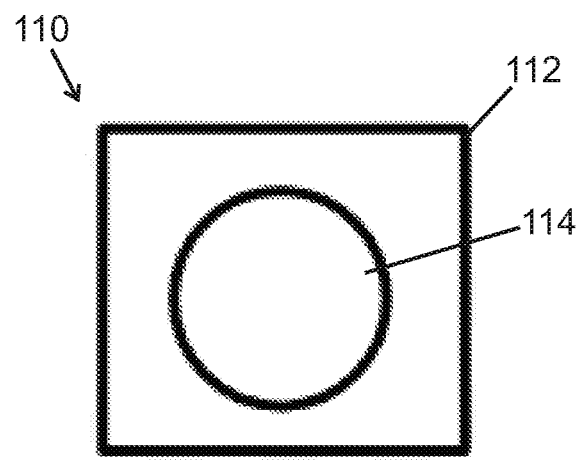

FIG. 9B is a schematic cross-sectional view of a portion of a fluidic device including a fluidic channel having a round cross-sectional shape, according to one embodiment.

Figure 9C:
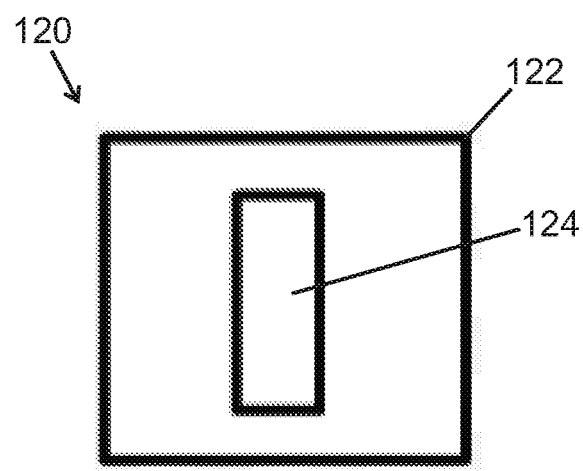

FIG. 9C is a schematic cross-sectional view of a portion of a fluidic device including a fluidic channel having a narrow rectangular cross-sectional shape, according to one embodiment.

Figure 10:
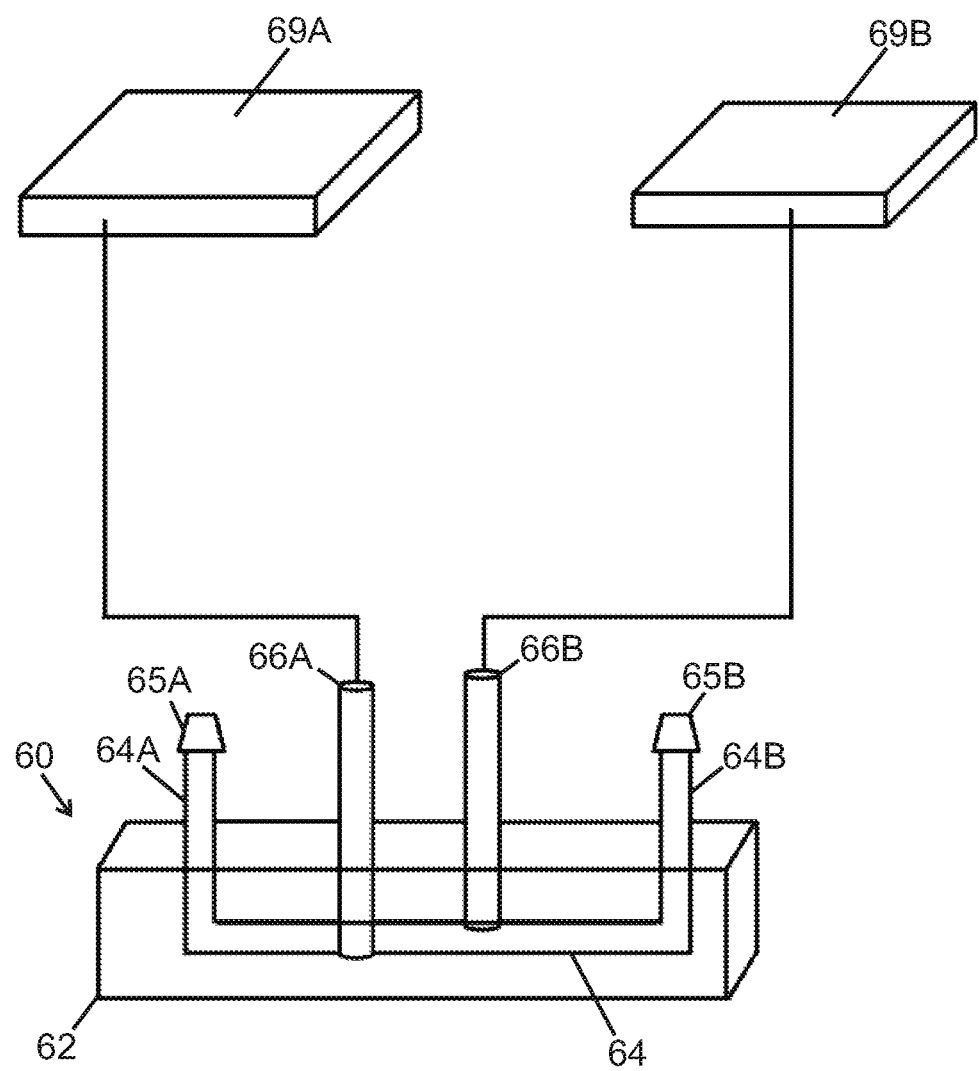

FIG. 10 is a schematic perspective view of a fluidic device according to FIG. 8B and electrodes connected to electrical contacts of a TDID system according to one embodiment.

Figure 11A:
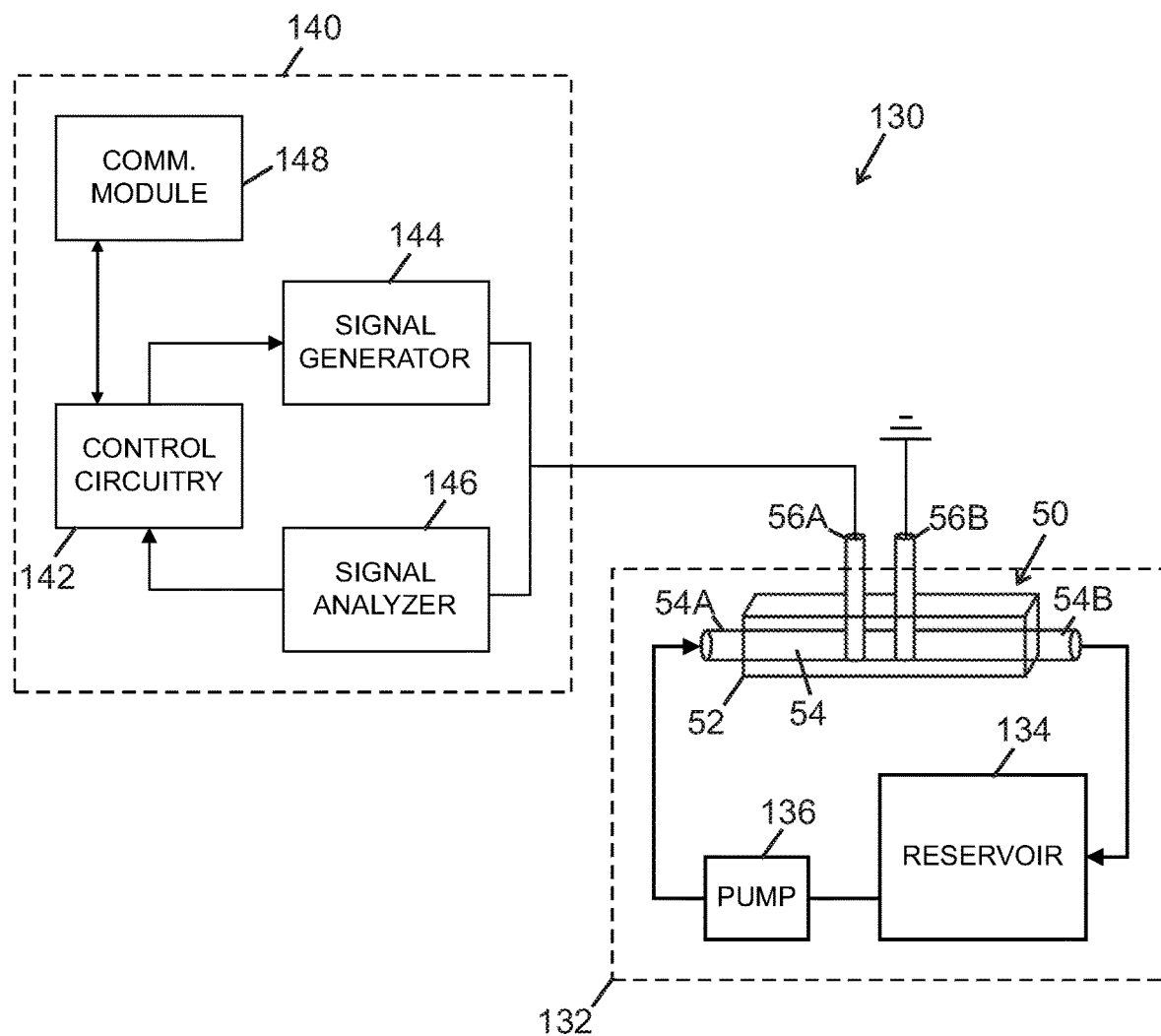

FIG. 11A is a schematic diagram showing electrical connections and fluidic connections of a TDID system including a fluidic device according to FIG. 8A, according to one embodiment.

Figure 11B:
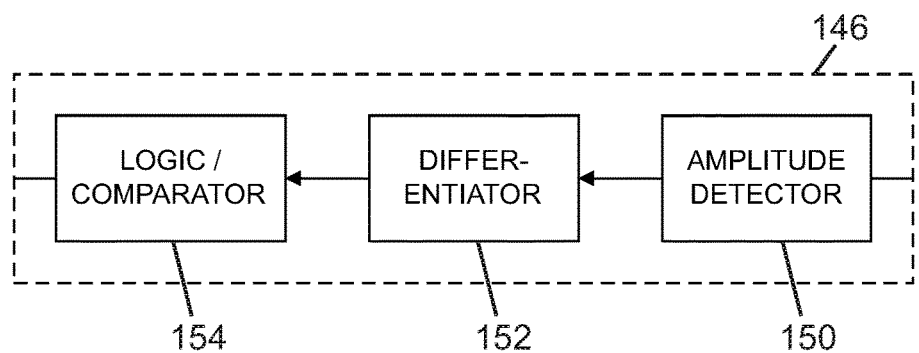

FIG. 11B is a schematic diagram showing subcomponents of the signal analyzer represented in FIG. 11A, according to one embodiment.

Figure 12A:
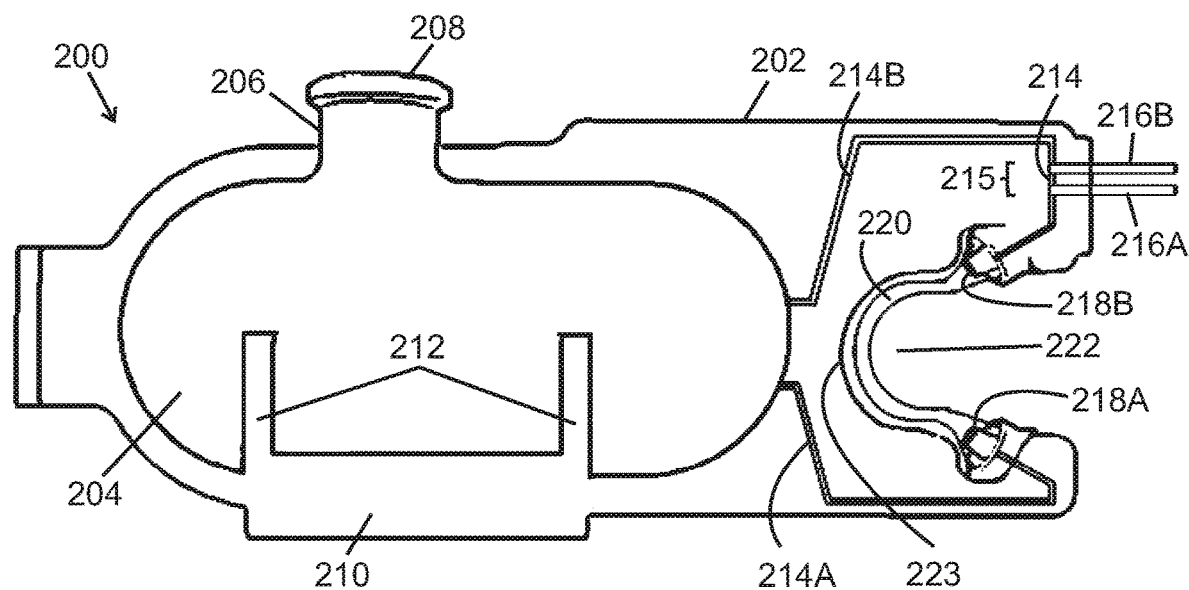

FIG. 12A is a side elevation view of an assembly including a reservoir, a sample analysis segment including electrodes in electrical communication with a measurement channel, a pump interface segment including a curved section of flexible tubing, and a fluidic circuit enabling circulation of a sample between the reservoir, the sample analysis segment, and the pump interface segment.

Figure 12B:
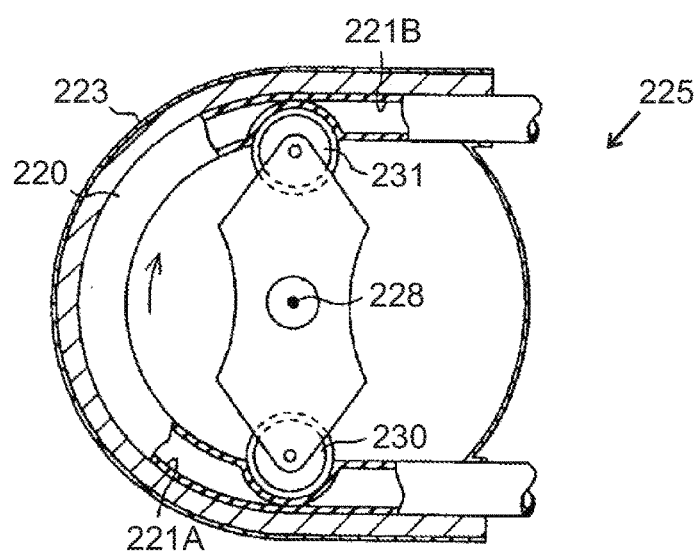

FIG. 12B is a side cross-sectional view of a portion of a rotary squeeze pump suitable for cooperating with the pump interface segment of the assembly of FIG. 12A.

Figure 13:
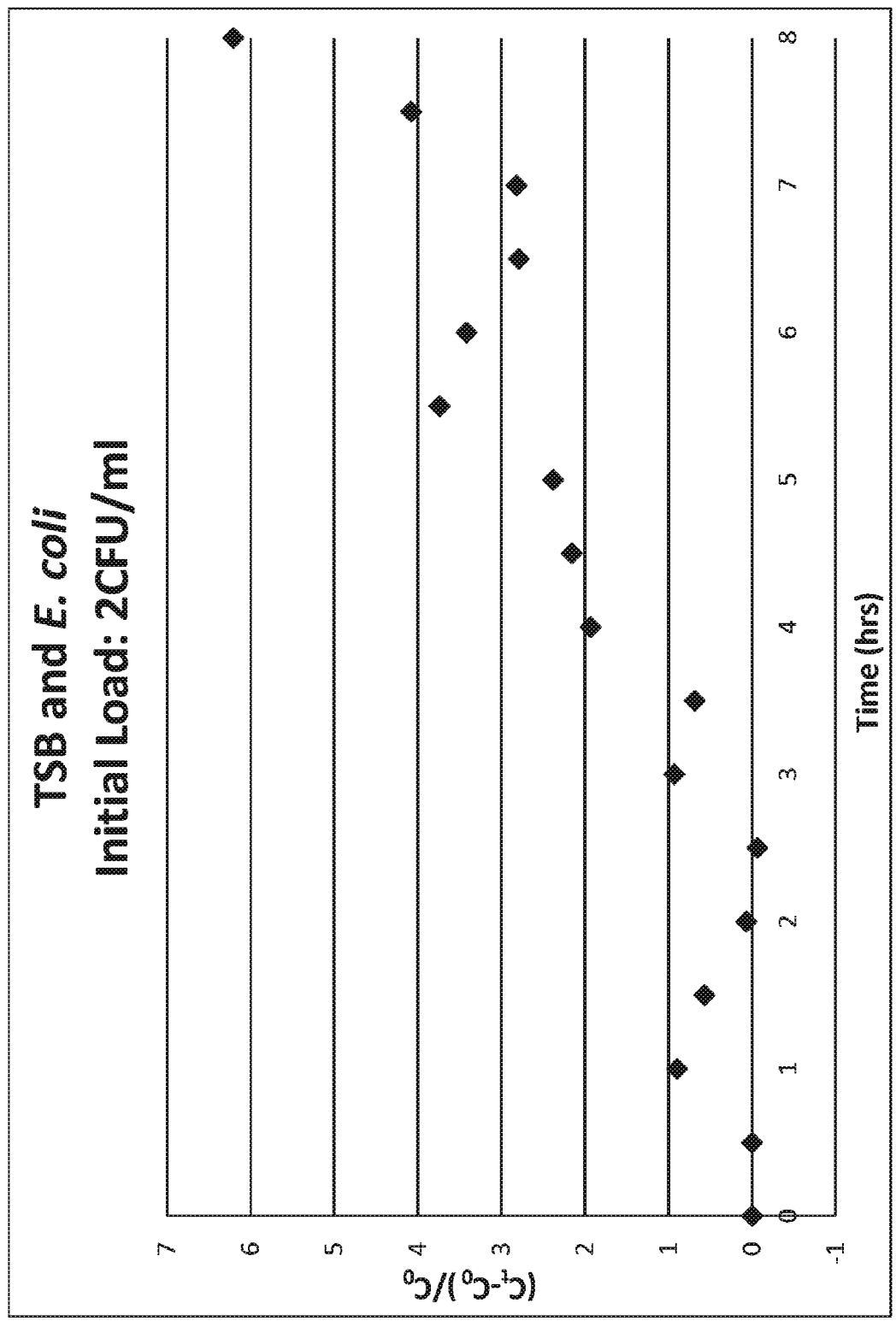

FIG. 13 is a plot of percentage change in parameter C versus time (hrs) for an 8 hour experiment utilizing a TDID system as disclosed herein with an initial bacterial load of 2 CFU/ml of *E. coli* (ATCC 25922) in Tryptic Soy Broth (TSB) (RPI Corp.).

Figure 14:
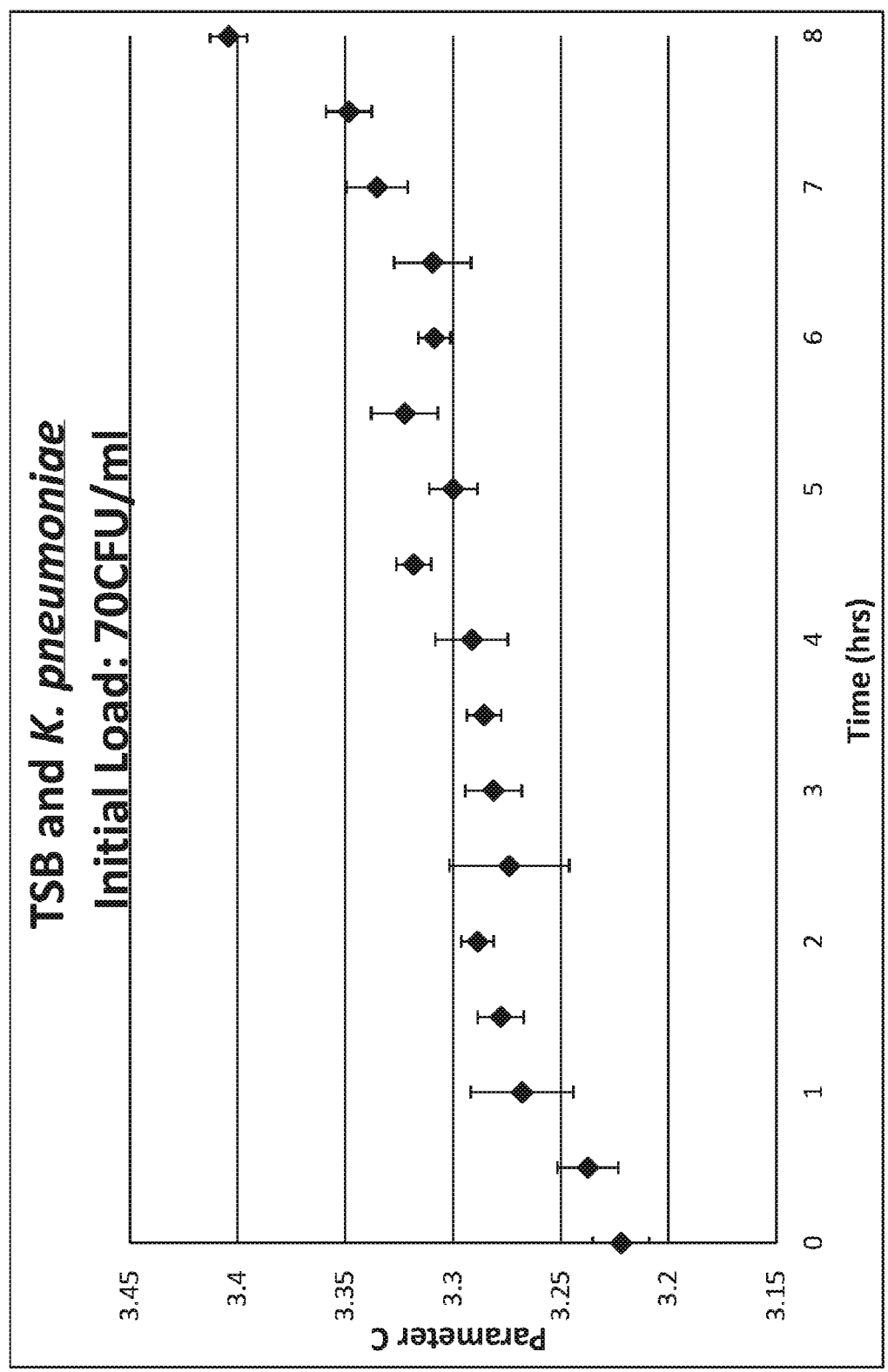

FIG. 14 is a plot of percentage of parameter C versus time (hrs) for an 8 hour experiment utilizing a TDID system as disclosed herein with an initial bacterial load of 70 CFU/ml of *K. pneumoniae* (ATCC 700603) in TSB.

Figure 15:
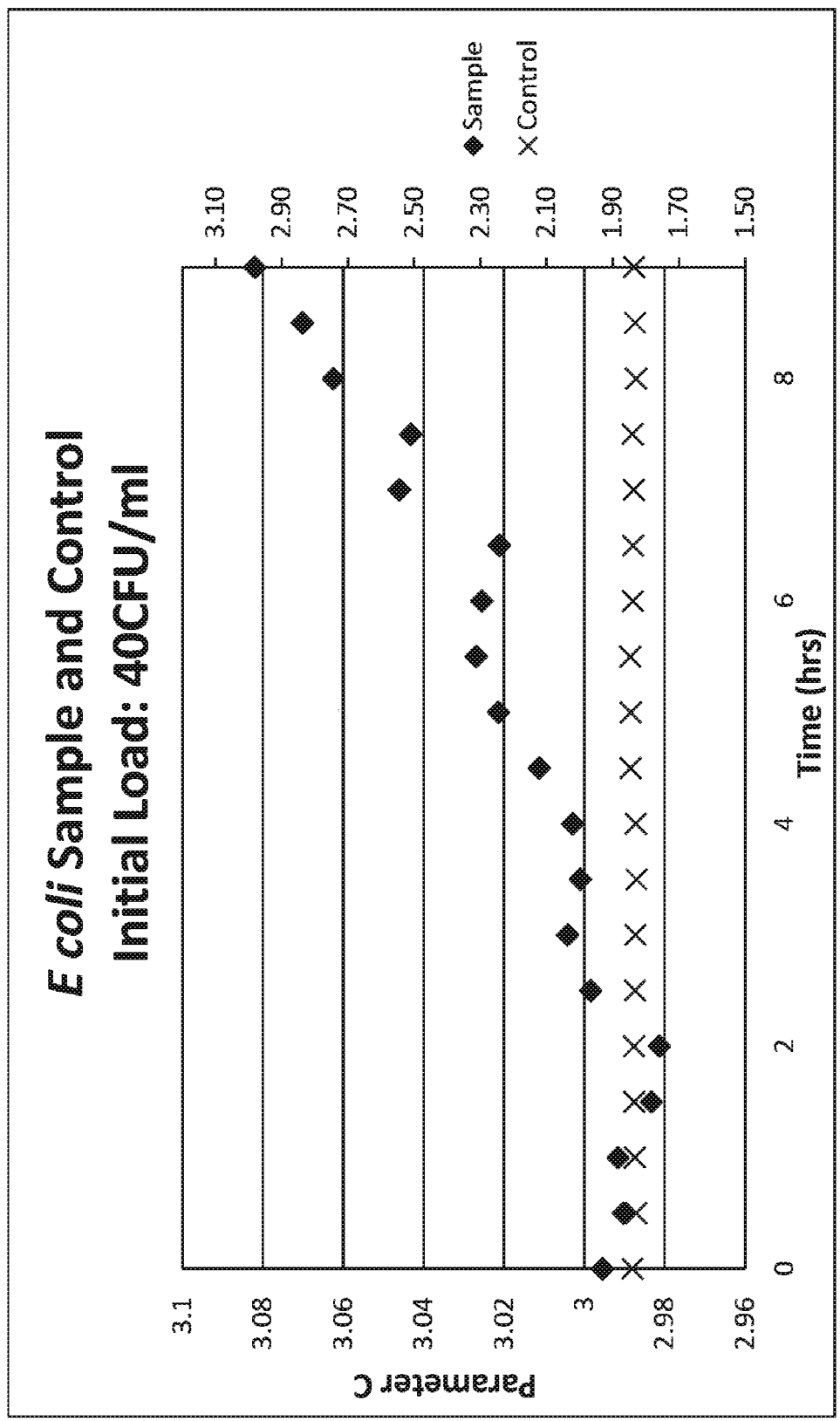

FIG. 15 is a plot of parameter C versus time (hrs) for a 9 hour experiment utilizing a TDID system as disclosed herein with an initial load of 40 CFU/ml (sample) of *E. coli* (ATCC 25922) in TSB, and TSB alone (control).

Figure 16:
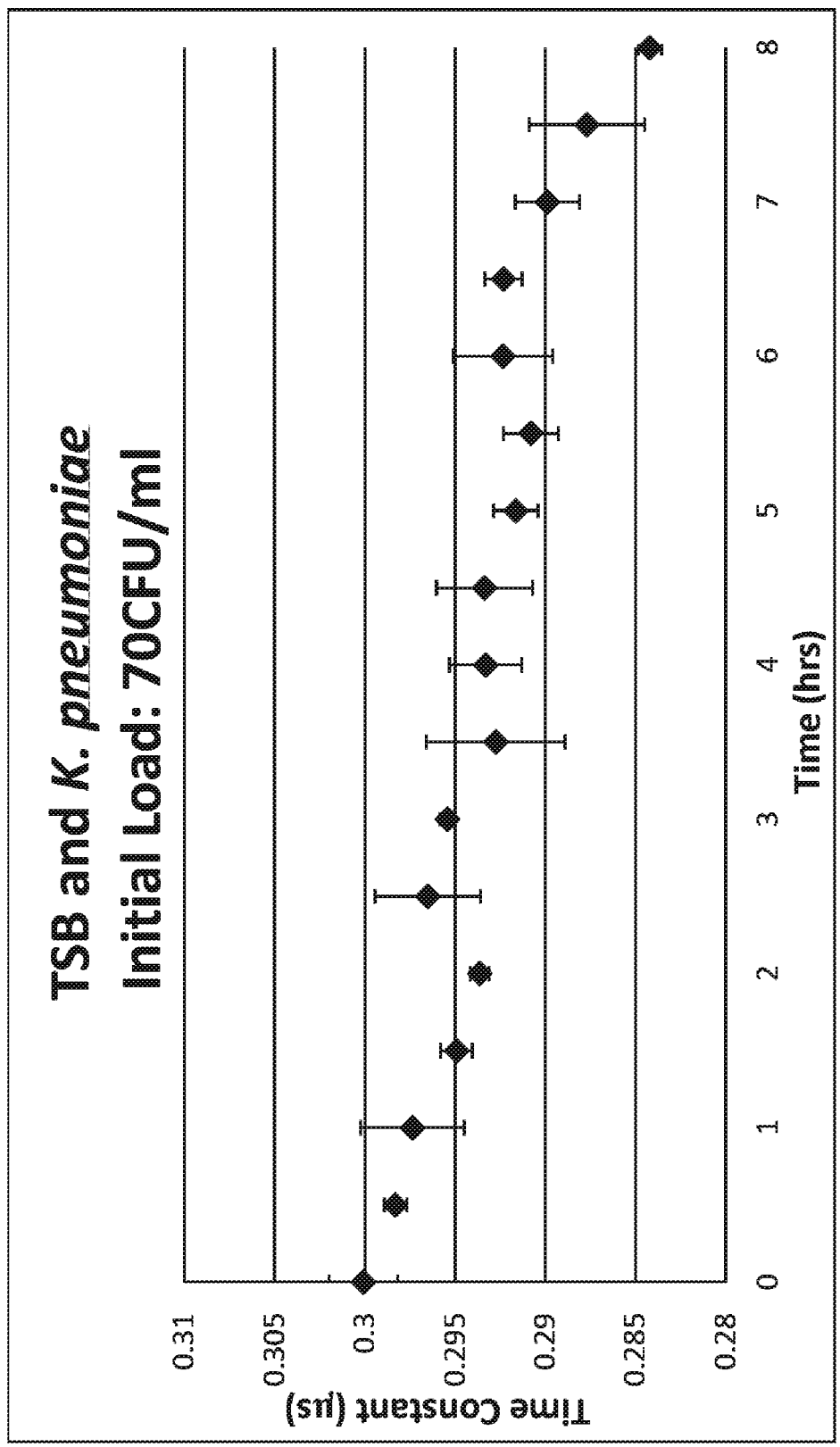

FIG. 16 is a plot of time constant (µs) versus time (hrs) for an 8 hr experiment utilizing a TDID system as disclosed herein with an initial load of 70 CFU/ml of *K. pneumoniae* (ATCC 700603) in TSB.

Figure 17:
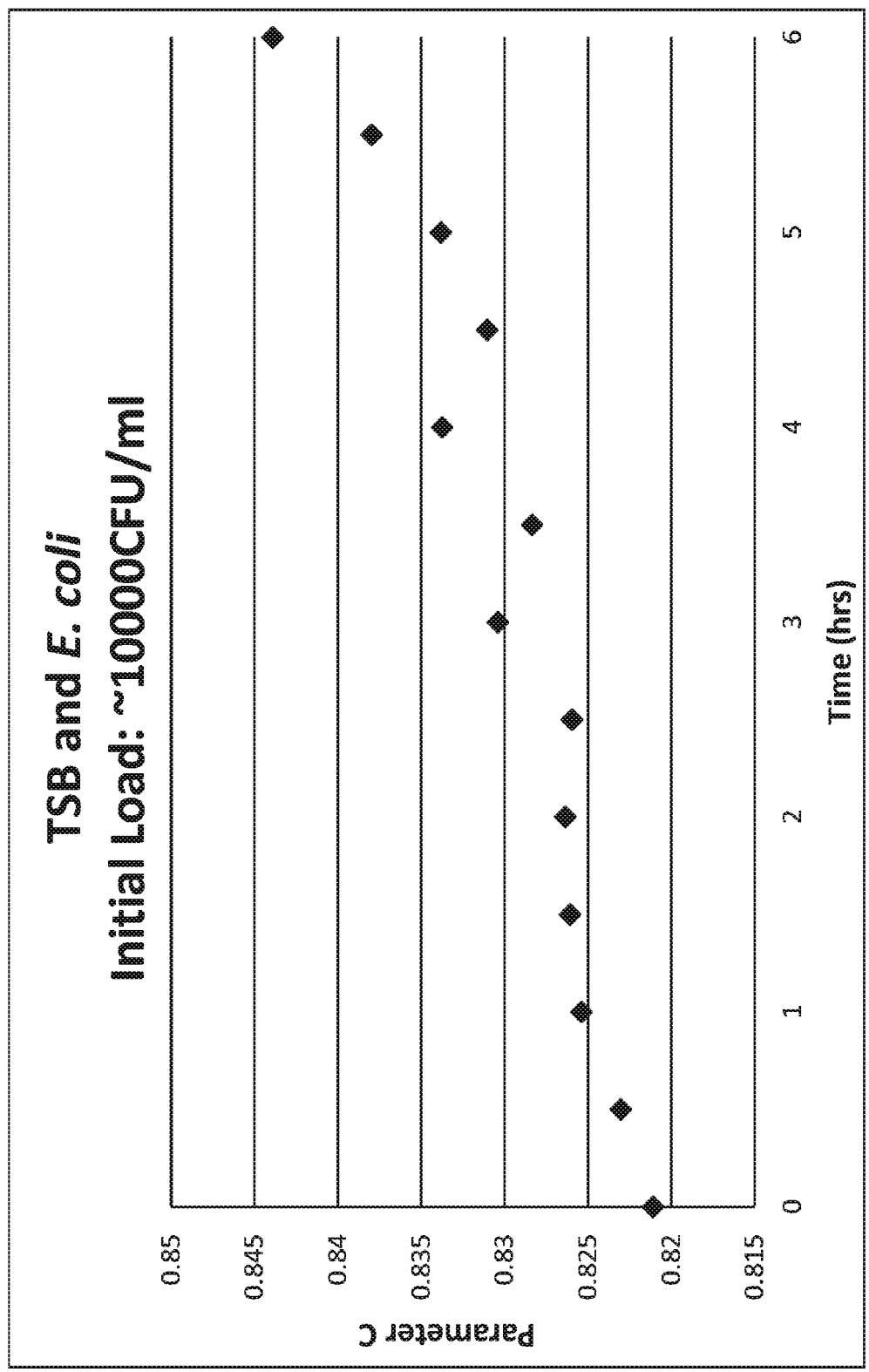

FIG. 17 is a plot of parameter C versus time (hrs) for a 6 hr experiment utilizing a TDID system as disclosed herein with an initial load of ~10000 CFU/ml of *E. coli* (ATCC 25922) in TSB.

Figure 18:
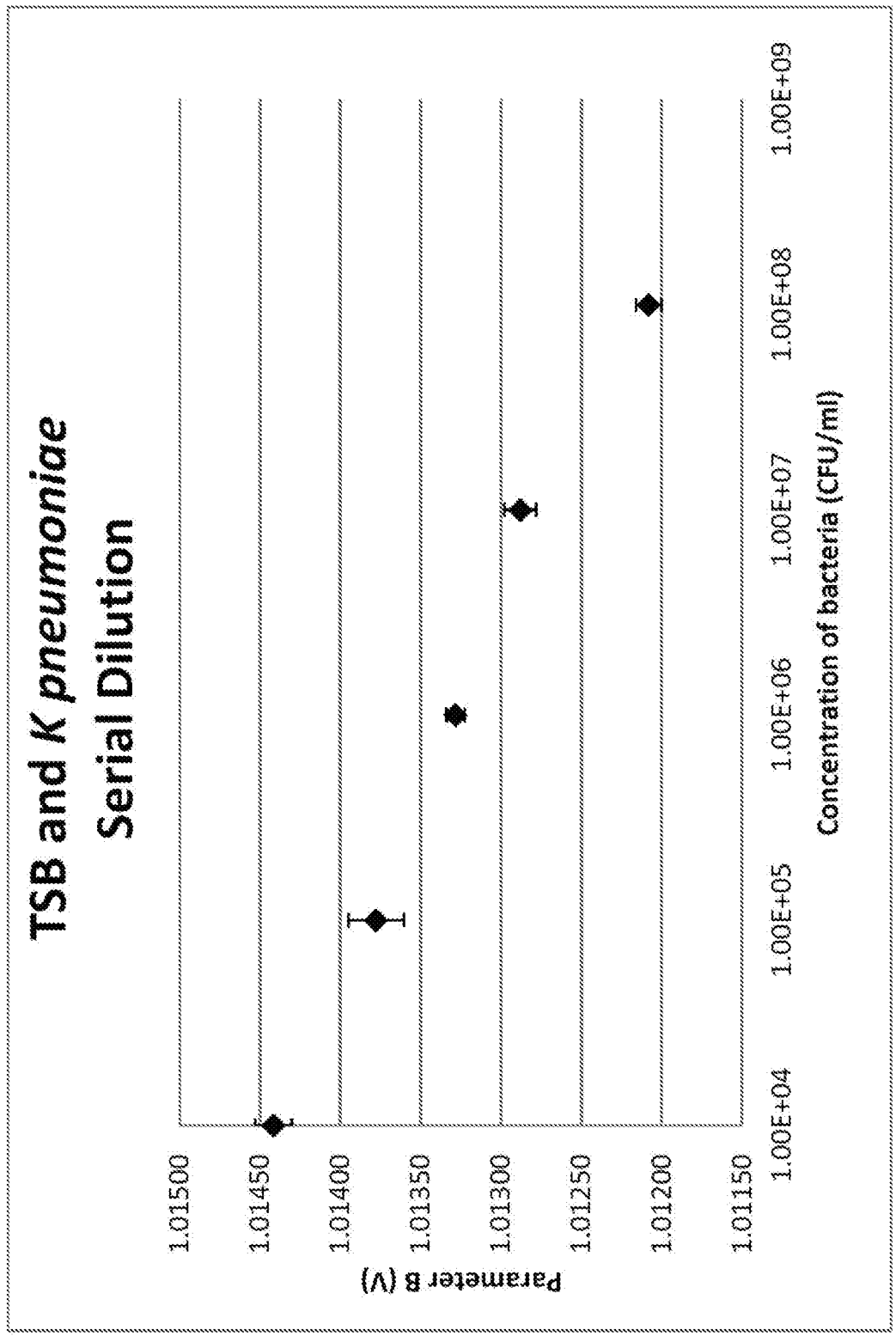

FIG. 18 is a plot of parameter B versus concentration of bacteria (CFU/ml) for a serial dilution experiment utilizing a TDID system as disclosed herein with *K pneumoniae* (ATCC 700603) in TSB.

Figure 19:
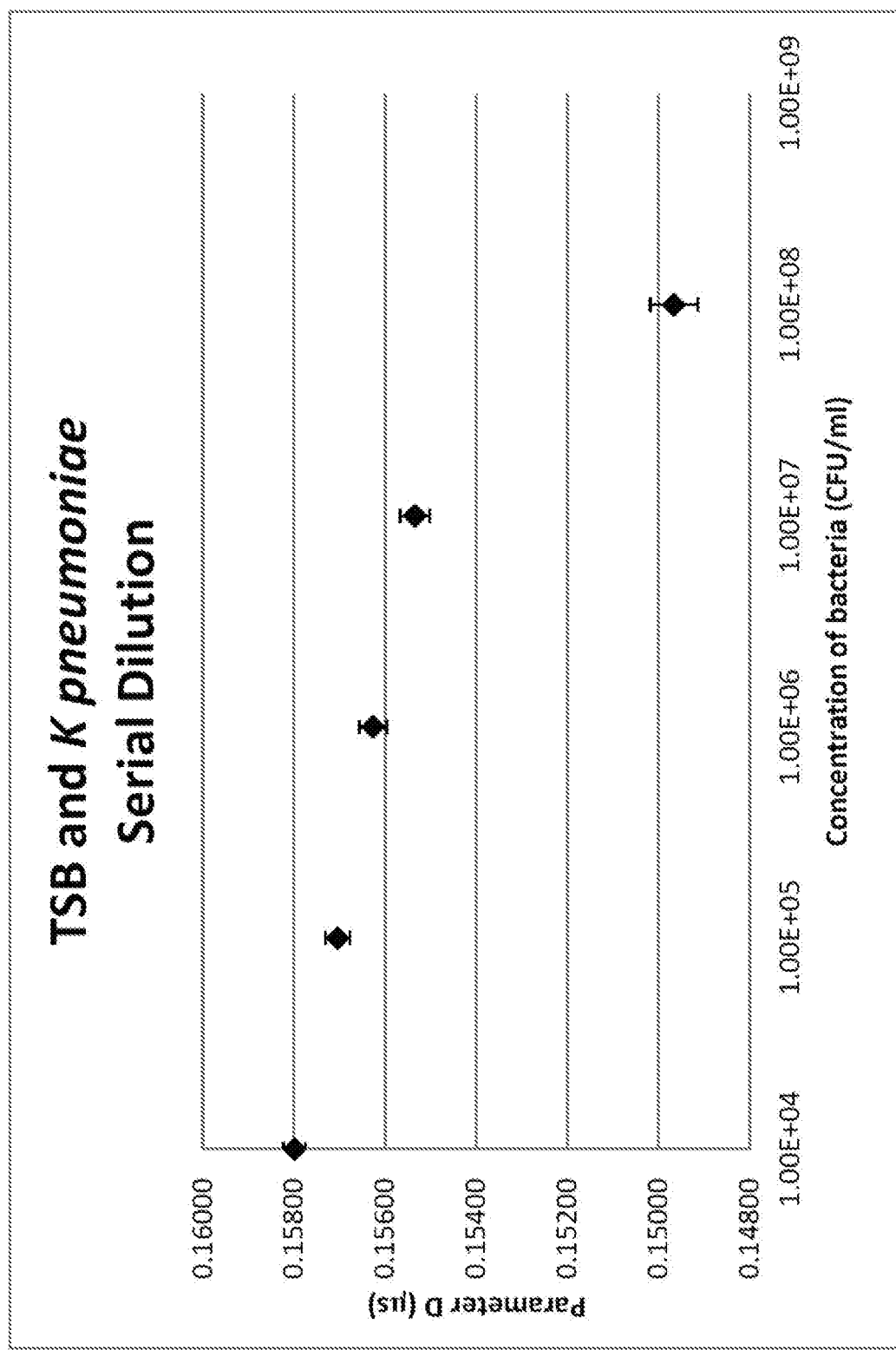

FIG. 19 is a plot of parameter D versus concentration of bacteria (CFU/ml) for a serial dilution experiment utilizing a TDID system as disclosed herein with *K pneumoniae* (ATCC 700603) in TSB.

Figure 20:
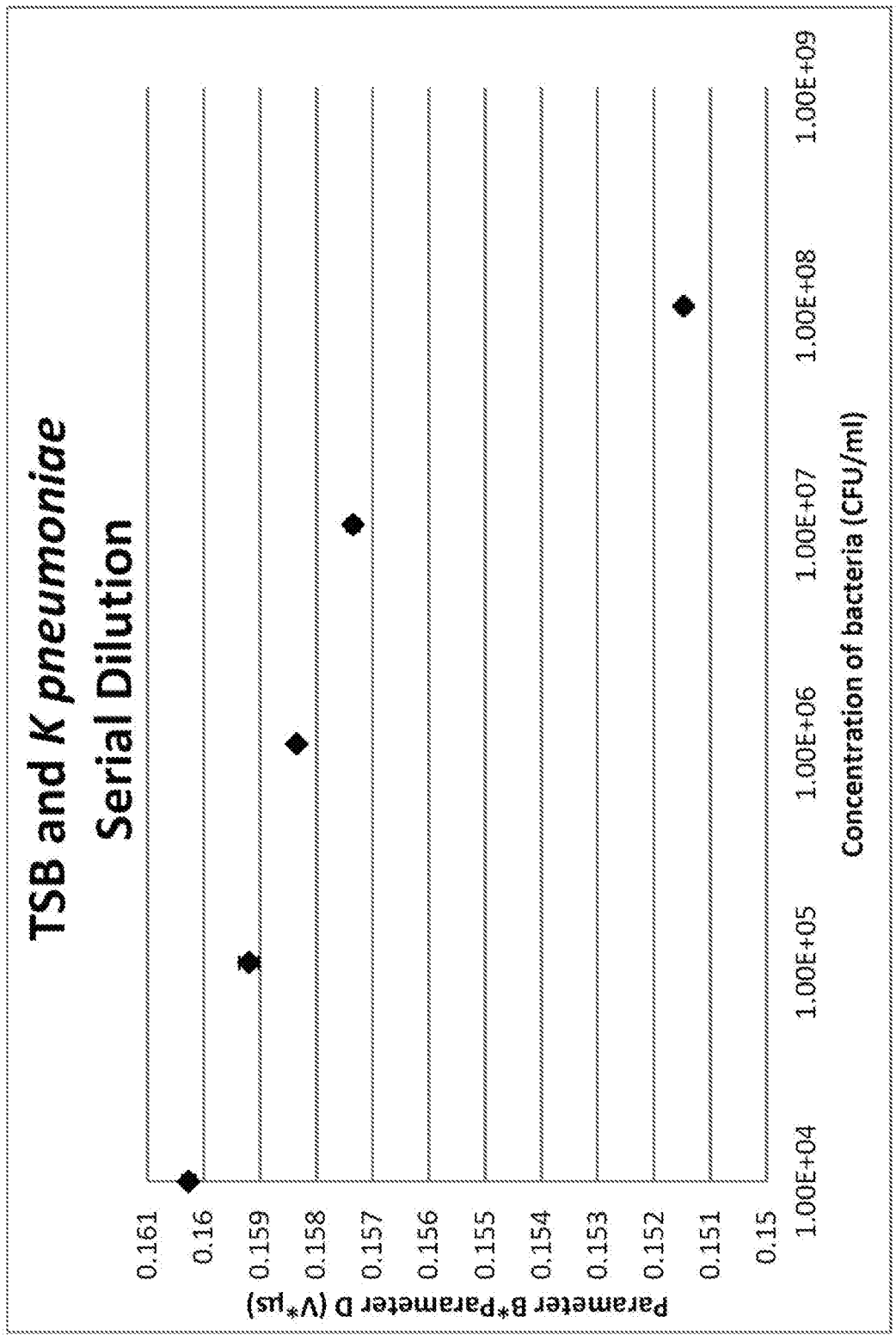

FIG. 20 is a plot of the product of parameter B and parameter D versus concentration of bacteria (CFU/ml) for a serial dilution experiment utilizing a TDID system as disclosed herein with *K pneumoniae* (ATCC 700603) in TSB.

Figure 21:
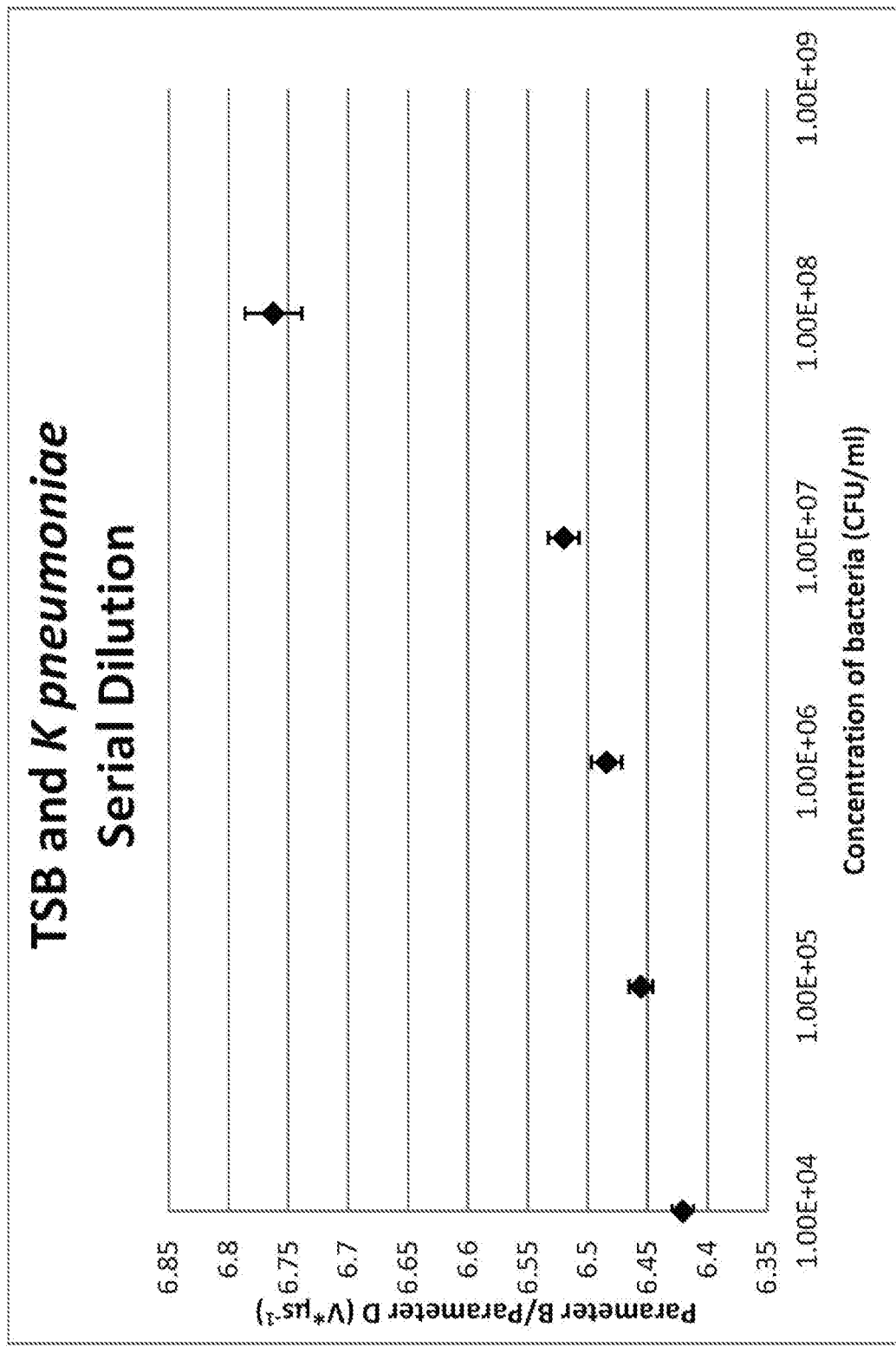

FIG. 21 is a plot of the quotient of parameter B and parameter D versus concentration of bacteria (CFU/ml) for a serial dilution experiment utilizing a TDID system as disclosed herein with *K pneumoniae* (ATCC 700603) in TSB.

Figure 22:
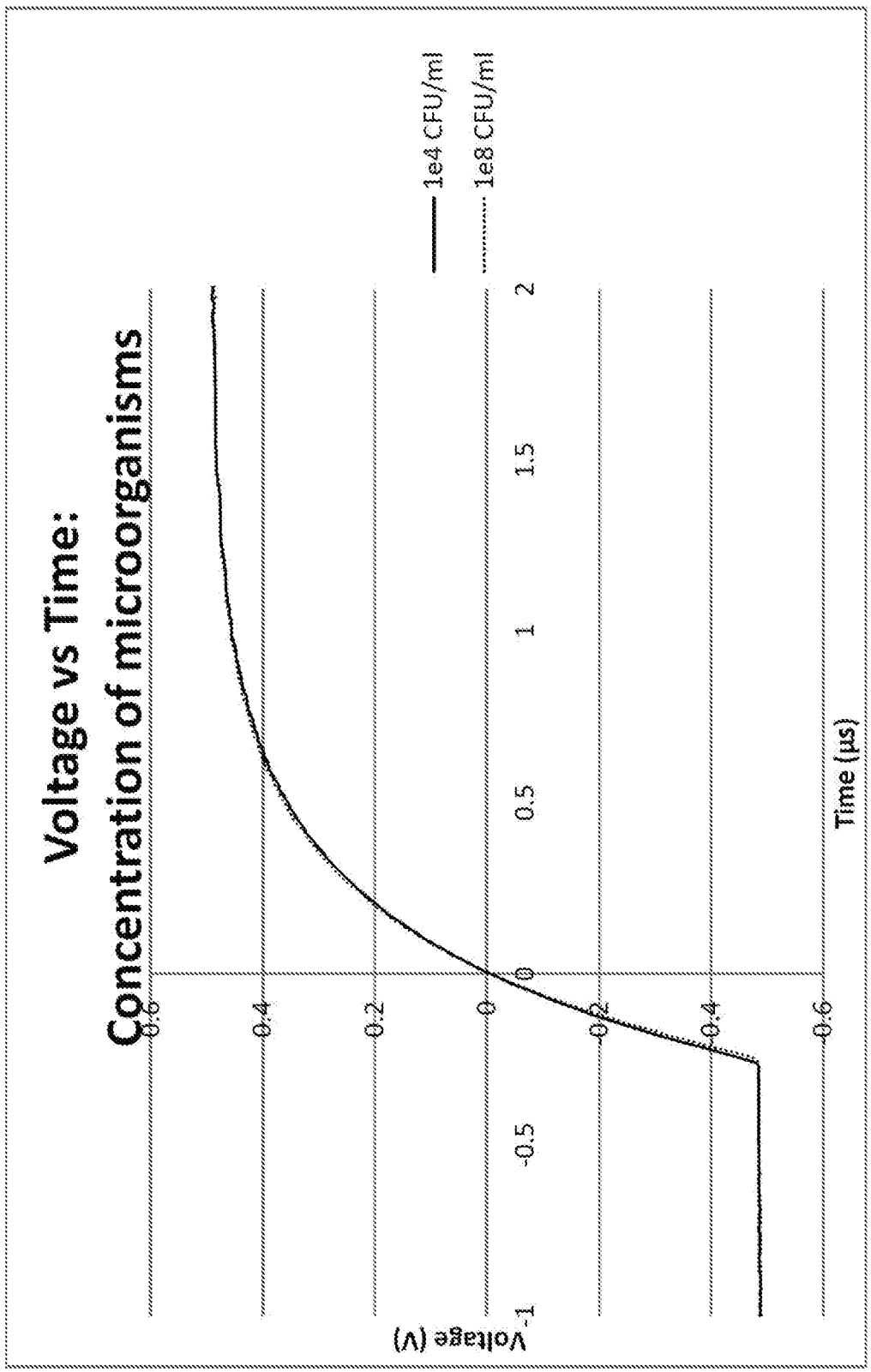

FIG. 22 is a plot of voltage (V) versus time (µs) for the averaged rising edge output (response) signals responsive to the application of twenty 1V DC pulses for two different concentrations ($10^4$ CFU/ml and $10^8$ CFU/ml) of *E. coli* in TSB obtained by utilizing a TDID system according to one embodiment.

Figure 23:
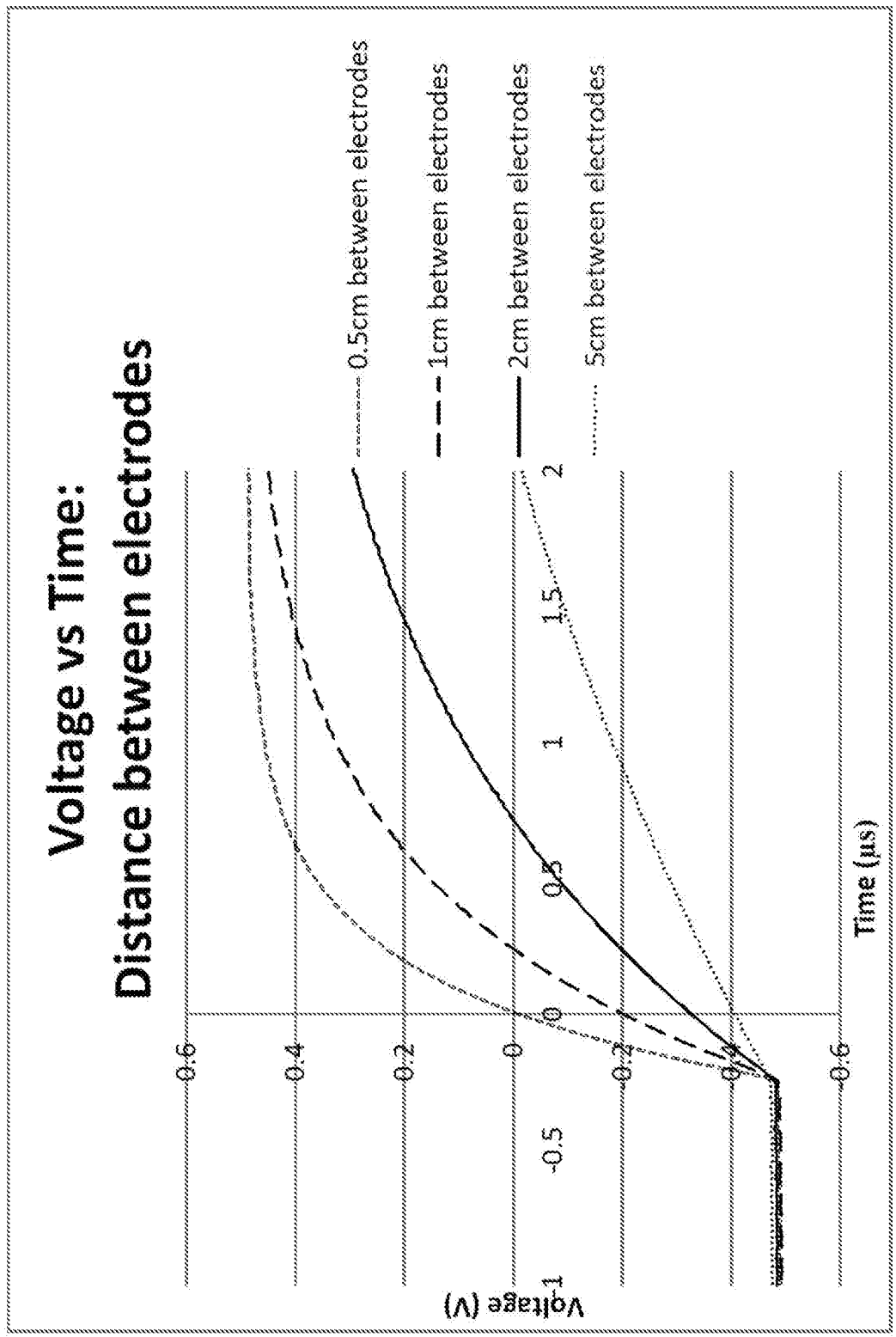
Figure 24:
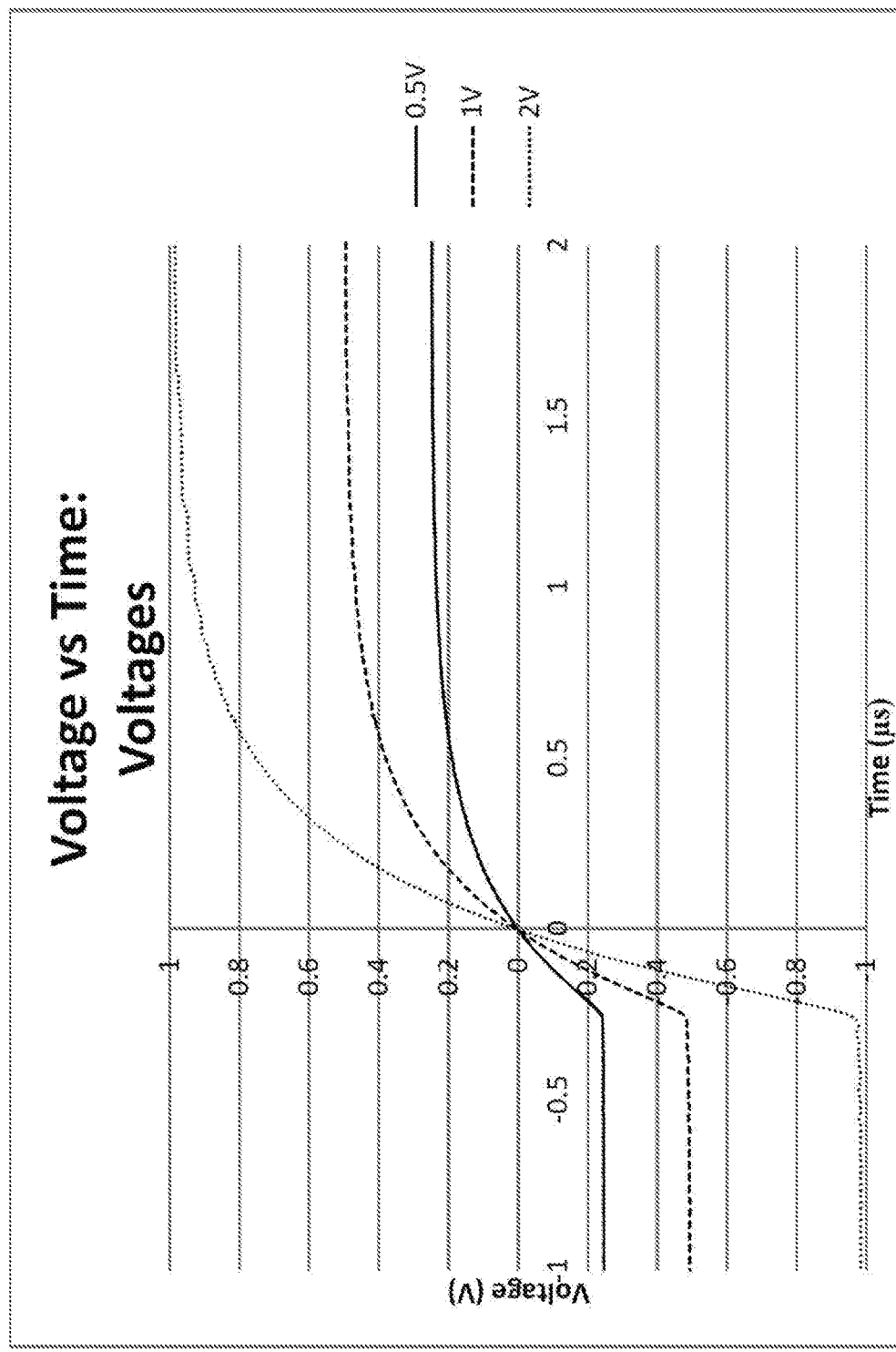

FIG. 23 is plot of voltage (V) versus time (µs) for the averaged rising edge output (response) signals responsive to the application of twenty 1V DC pulses for TSB in four measurement channels with different distances between the two electrodes (0.5 cm, 1 cm, 2 cm, and 5 cm) obtained by utilizing a TDID system according to one embodiment FIG. 24 is plot of voltage (V) versus time (µs) for the averaged rising edge output (response) signals responsive to the application of twenty DC pulses with three different applied voltages (500 mV, 1V, and 2V) obtained by utilizing a TDID system according to one embodiment

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

The term "pathogen" as used herein refers to a disease-causing microorganism, and includes, but is not limited to, bacteria, viruses, fungi, yeasts, and molds.

The present disclosure provides a system and method for rapid detection of viable microorganisms (e.g., pathogens) in liquid media suspensions. At least two electrodes are placed in electrical communication with liquid media possibly containing microorganisms. When a first electrical pulse is applied across the at least two electrodes at an initial time, a first initial electrical response signal is generated, with such signal being indicative of electrical response in a short first initial time window (e.g., no longer than a time required to attain 95% (or another threshold percentage disclosed herein) of a steady state electrical response value after a change in state of the first electrical pulse). Thereafter, when a second electrical pulse is applied across the at least two electrodes at a subsequent time, a second initial electrical response signal is generated, with such signal being indicative of electrical response in a short second initial time window (e.g., no longer than the time required to attain 95% (or another threshold percentage disclosed herein) of the steady state electrical response value after a change in state of the second electrical pulse). Changes in electrical response between the subsequent time and the initial time, which may be measured electronically, may evidence proliferation of one or more pathogens in the liquid media. Such pathogens may include bacteria, viruses, fungi, yeast, spores, and/or other non-mammalian cells. In general, non-mammalian cells will have a different membrane potential than mammalian cells. Thus, they will affect the overall electrical response and/or electronic signature of the solution differently than mammalian cells in response to application of an electrical pulse.

Without being bound by any specific scientific theory underpinning the methods disclosed herein, it is currently believed that utilization of initial electrical response signals corresponding to very short time windows (e.g., no longer than the time required to attain 95% (or another threshold percentage disclosed herein) of the steady state electrical response value or some other threshold identified herein) after a change in state of an electrical pulse permits bulk electrical properties of a suspension to be determined because double layer formation at an electrode-liquid interface may be incomplete during such time windows. In certain embodiments, such time windows may be no longer than a time required to attain 98%, 95%, 90%, 85%, 80%, 75%, 70%, 65%, 60%, 55%, or 50% of a steady state electrical response value. As noted previously, capacitance at a solid-liquid interface between an electrode and a suspension is dramatically larger than the bulk capacitance of a liquid suspension between two such electrodes, such that it can be difficult to detect a small change in capacitance attributable to pathogen proliferation against the backdrop of a much higher (e.g., 1000 times higher) baseline capacitance attributable to presence of double layers on the electrodes. Applicant has found that by utilizing initial electrical response signals corresponding to very short time windows after a change in state of an electrical pulse (presumably before double layer formation is complete and steady state electrical response is obtained), electrical properties of a bulk solution can be determined. By repeating the same measurement over time, a change in electrical response can be identified and used to detect the presence (i.e., by proliferation) of microorganisms such as pathogens in liquid suspensions. In certain embodiments, a bulk solution is maintained at conditions conducive to growth of microorganisms during one or more time periods spanning between measurements.

Steady state electrical response is obtained after complete double layer formation, following a change of state in an electrical pulse. "Steady state electrical response" refers to an equilibrium condition of a circuit that occurs as the effects of transients are no longer important. It is believed that steady state electrical response according to systems and methods described herein is asymptotic in character, wherein a significant change in electrical response is obtained immediately after a change of state of an electrical pulse, but such change in response diminishes as electrical response approaches a steady state condition. For example, if a change of state includes application of an electrical pulse, then an electrical response characteristic (e.g., pseudo-capacitive in nature) may rise quickly (e.g., in an exponential manner) with an highly positive initial slope having a value much greater than 1, but such slope will diminish with time until it reaches zero (i.e., steady state). Conversely, if a change of state includes termination of an electrical pulse, then an electrical response characteristic (e.g., pseudo-capacitive in nature) may fall quickly (e.g., in an exponential manner) with a highly negative initial slope value, but such slope will become less negative with time until it reaches zero (i.e., steady state). Use of initial electrical response signals corresponding to very short time windows after a change in state of an electrical pulse, prior to attainment of steady state conditions, permits electrical properties of a bulk solution to be determined.

As noted previously, system configuration differences and/or operational parameters (e.g., electrode size, electrode position/spacing, electrode surface quality, overall channel or chamber dimensions, system fouling, voltage and/or current values, pulse shape, etc.) may affect electrical response, so the time to attainment of steady state condition may be different for systems that entail different configurations or operational parameters. To address this issue, in certain embodiments described herein, duration of initial time windows (in which electrical properties of a bulk solution may be determined) may be defined in terms of time required to attain a specified percentage (below 100%) of a steady state electrical response value. In certain embodiments, to ensure that sufficient electrical response information is collected, an initial time window may be further bounded by a minimum duration, such as longer than a time required to attain at least about 2%, at least about 5%, at least about 10%, at least about 15%, at least about 20%, at least about 25%, or at least about 30%, of a steady state electrical response value. Thus, in certain embodiments, initial electrical response signals useful with systems and methods disclosed herein may correspond to minimum time windows after a change in state of an electrical pulse that are at least as long as times corresponding to attainment of one or more minimum duration thresholds disclosed herein, but that are no longer than times corresponding to attainment of one or more maximum duration thresholds disclosed herein, with both minimum and maximum duration thresholds corresponding to percentages of time to attainment of steady state electrical response values. In certain embodiments, initial time window duration values may optionally be within one or more of the following ranges: 1-1000 nanoseconds, 5-800 nanoseconds, 10-700 nanoseconds, 20-600 nanoseconds, 30-500 nanoseconds, 35-400 nanoseconds, 40-300 nanoseconds, or 50-200 nanoseconds.

One potential issue with respect to seeking to identify change suggesting microorganism proliferation by taking multiple electrical measurements over time of a bulk suspension (or portions thereof) is that changes in electrical response of the bulk suspension may be attributable at least in part to phenomena other than microorganism proliferation—such as changes in pH, salt concentration, chemical composition, peptide/protein concentration, presence of red and/or white blood cells, and/or other parameters of the liquid media of the bulk suspension. Such changes to the liquid media may be byproducts of microorganism proliferation and/or induced by other causes. Additionally, different bulk solutions (e.g., derived from different samples) may have different starting properties, such as salt concentration, pH, chemical composition, peptide/protein concentration, or the like. To address these issues, in certain embodiments, measurements taken over a more extended time period (e.g., including a time period after formation of a double layer at each electrode) may be used to detect electrical response of the entire composition of the bulk suspension (including liquid media as well as microorganisms), and this extended electrical response may be used to normalize the above-described initial electrical response signals obtained during a short initial time window after change in state of a pulse. Utilization of initial and extended electrical response measurements allows for greatly increased sensitivity in detection of microorganisms (e.g., pathogens) in bulk suspensions. In certain embodiments, as baseline measurements are made, the starting properties of bulk suspensions can be normalized to the overall measurement technique. For example, if two different bulk suspensions have different starting concentrations of salt, the overall resistance of each bulk suspension will be different. In certain embodiments, pH, salt concentration, chemical composition, peptide/protein concentration, and/or other parameters of liquid media of a bulk suspension may change from an initial measurement to a subsequent measurement of electrical response. Utilization of an extended time period (or simply "extended") electrical response to normalize an initial time period (or simply "initial") electrical response permits inter-sample and intra-sample differences to be normalized. Moreover, systems and methods disclosed herein allow numerous measurements to be rapidly generated at a rate greater than 1 measurement per second. Thus, baseline measurements of a starting solution can be quantified and mathematically modeled to a high degree of positivity. As pathogens present in the media proliferate, measurable changes in both liquid media properties and pathogenic charge storing properties of the bulk suspension are subject to change against this baseline and are detectable using methods and systems disclosed herein more rapidly than through use of conventional techniques. In certain embodiments, an extended time window may comprise an integer multiple of an shorter initial time window, such as a multiple of at least 2, 4, 6, 8, 10, 15, 20, 25, 30, 40, 50, 60, 80, 100, 150, 200, 250, 500, 750, or 1000.

Systems and methods disclosed herein enable detection of viable microorganisms more rapidly with simpler and less expensive circuitry as compared to previously methods. As noted previously herein, the Sengupta patent discloses frequency domain impedance sensing, in which hundreds of in-phase resistance (R) and out of phase reactance (X) values are obtained over a wide frequency range using AC input signals, and such sensing is repeated over multiple time intervals to enable determination of changes in bulk capacitance of a suspension to indicate proliferation (and therefore presence) of viable bacteria in the suspension. Although the method disclosed by the Sengupta patent is sensitive, it requires expensive instrumentation (e.g., a variable frequency impedance analyzer), and the method is relatively slow (e.g., requiring a period of minutes for each sample analysis).

In contrast to the methods disclosed by the Sengupta patent, methods disclosed herein involve time domain impedance sensing, without requiring AC signals to be applied to suspensions at numerous different frequencies. Methods disclosed herein can analyze suspensions much more rapidly with DC input signals. For example, in certain embodiments, DC pulses having a pulse width of 100 kHz may be used, thereby allowing impedance measurements to be taken every 10 microseconds.

In certain embodiments, time based response of a system may be monitored in response to application of a voltage pulse to a bulk suspension. This can be mathematically represented as:

$$V = V_0 (1 - e^{-t/\tau})$$

where $V_0$ is the amplitude of the input signal, t is the time, and $\tau$ is the time constant of the signal produced. As will be recognized by a person skilled in the art, other mathematical models can be used to track the changes in the overall electronic properties of a system disclosed herein. Certain examples include using curve-fitting equations such as: $y = a + b(1 - e^{-cx})$, $y = a + b(1 - e((x + c(\ln 2)^{1/d} - b)/(c))^d)$, and $y = a + ((bc(e^{-cx}) - e^{-dx})/(d - c))$; however, one skilled in the art will recognize that other curve-fitting equations can also be used. In each of these equations, parameters mathematically represent various electronic properties, such as amplitude, minimum voltage, maximum voltage, exponential growth, etc. A change in a parameter or a combination of parameters over time represents a change in the electronic properties of the suspension, which in turn represents microorganism (e.g., pathogen) growth. Area under a curve may be determined through mathematical relationships of different parameters. In certain embodiments, area under a curve is represented by the division of two parameter values. Parameters and combinations of parameters can all be plotted versus time. Changes in such values over time may indicate changes in electronic properties of the suspension.

Figure 2:
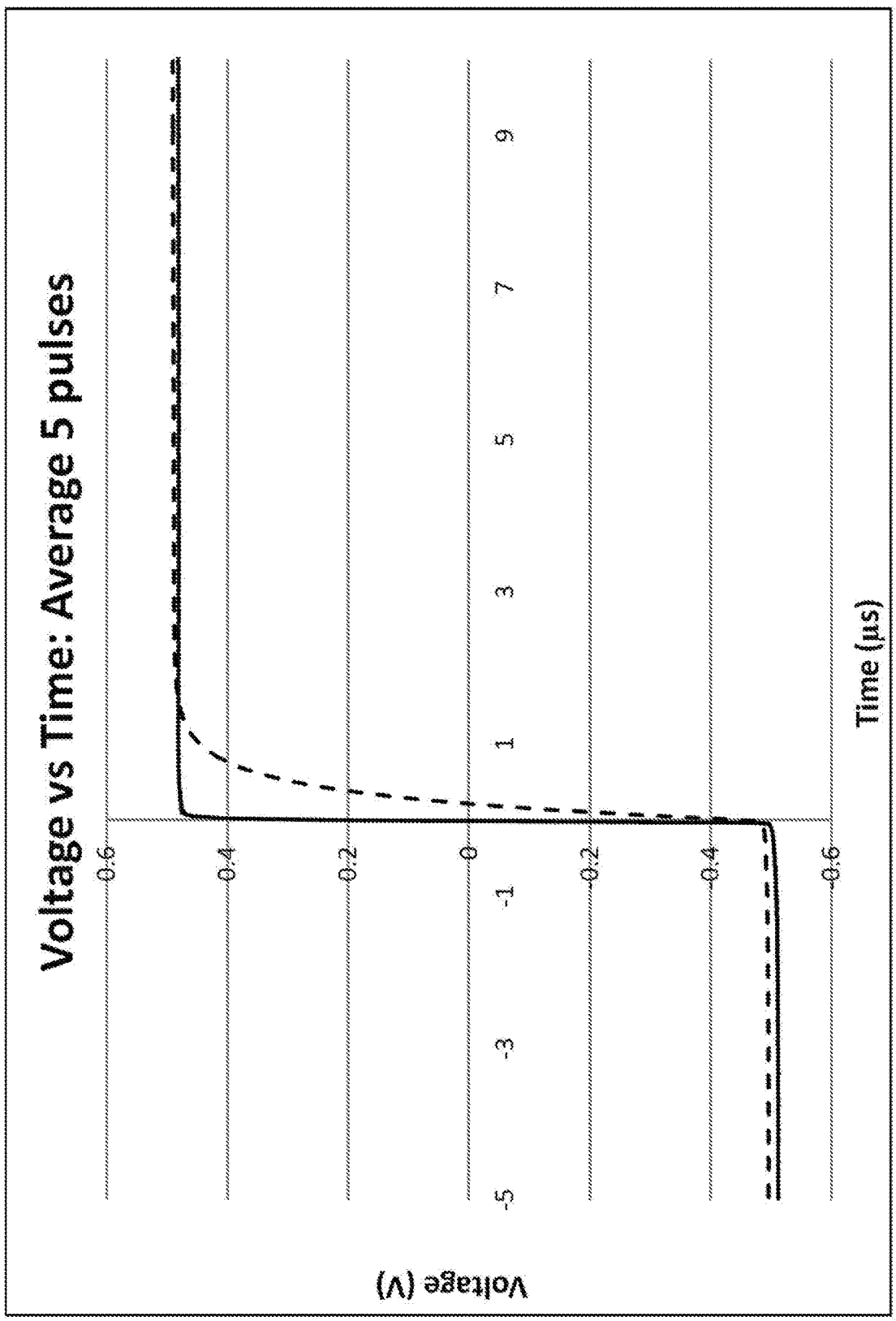
FIG. 2 provides superimposed plots of voltage versus time for (i) an ideal rising edge for a 1V DC pulse, and (ii)

In certain embodiments, a measurement window is initiated by a change in state of an electrical pulse that comprises a current rise or a voltage rise. Restated, such a measurement window may correspond to initiation of a pulse. FIG. 2 provides superimposed plots of voltage versus time for (i) an ideal rising edge for a 1V DC pulse (represented as a solid line) supplied as an input to electrodes of a TDID system, and (ii) averaged rising edge output (response) signals (represented as a dashed line) responsive to application of five 1V DC pulses using a TDID system according to one embodiment. The averaged rising edge output or response signal embodies a curve that differs in shape from the curve of the ideal rising edge input signal, and is subject to being mathematically modeled according to a curve-fitting equation as outlined above.

FIG. 3A provides superimposed plots of voltage versus time for a rising edge of a 1V DC pulse output by a TDID system according to one embodiment, including (i) raw output voltage (points) and (ii) curve-fitted output voltage (solid line), over a 10 μs timeframe. FIG. 3B provides superimposed plots of voltage versus time for a rising edge of the same 1V DC pulse output as FIG. 3A, including (i) raw output voltage (points) and (ii) curve-fitted output voltage (solid line), over a 50 μs timeframe. A comparison of these figures reveals that the voltage response resembles a curve (as shown in FIG. 3A) when viewed within an appropriately short timeframe, despite more closely resembling a square wave (as shown in FIG. 3B) when viewed within a longer timeframe.

In certain embodiments, a measurement window is initiated by a change in state of an electrical pulse that comprises a current drop or a voltage drop. Restated, such a measurement window may correspond to termination of a pulse. FIG. 4 is a plot of average voltage versus time for falling edges of five 1V DC pulses (corresponding to termination of a DC input signal) obtained using a TDID system according to one embodiment. The averaged output or response signal embodies a curve that differs in shape from a corresponding input signal (not shown, but representable as an instantaneous drop from 0.5V to −0.5V), and is subject to being mathematically modeled according to a curve-fitting equation as outlined above.

Thus, in various embodiments, measurement windows may be initiated by changes in state of electrical pulses that comprise a rise (or initiation) in current or voltage, or that comprise a drop (or termination) in current or voltage. In theory, either initiation or termination of an electrical pulse should enable measurement of a comparable response of electrodes and a bulk solution. In practice, however, reduced noise may result when measurement windows are initiated by a change in state of an electrical pulse corresponding to a current drop or a voltage drop, since the phenomena of overshoot and ringing (i.e., unwanted oscillation of voltage or current) are inherent to application of a pulse using real-world (non-idealized) circuits, but such phenomena may be absent when a pulse is terminated. Differences between application and termination of electrical pulses are apparent upon comparison of FIGS. 5A and 5B. FIG. 5A is a plot of voltage versus time generated by a circuit board for a rising edge of a 1V DC pulse corresponding to a voltage rise, showing the circuit as exhibiting ringing (oscillation) for several microseconds until voltage is stabilized at a 1V value. FIG. 5B is a plot of voltage versus time generated by a circuit board for a trailing edge of a 1V DC pulse corresponding to a voltage drop, with the trailing edge being free from ringing. It is to be noted that magnitude and/or duration of voltage oscillation in FIG. 5A may be reduced through conventional means, as it is difficult to fully eliminate ringing upon initiation of an electrical pulse.

Despite the foregoing discussion of mathematical fitting, in certain embodiments, no mathematical fitting (e.g., curve fitting) is performed. Instead, direct measurements of electrical signals can be performed to measure the time response of the system to the input signal. For example, in one embodiment, a voltage comparator may be used to determine the rise time of a signal upon application of a pulse. In such a case, mathematical fitting is not necessary. Instead, a comparator may measure a difference between the input voltage and a resulting voltage obtained via electrodes wetted with a suspension, and a delay time between the input voltage (pulse) and resulting voltage. A comparator can be set to a variety of levels, depending on the desired outcome. In certain embodiments, a comparator may be set to report a time delay between the start of an input pulse and a state in which the output signal is 66% of the total maximum (input) signal, wherein the resulting time delay would represent the time constant of the system. For example, FIG. 6 shows the same voltage versus time data plot (without curvefit) as FIG. 3B, modified to include a first (lower) horizontal arrow corresponding to an initial "base" voltage (−0.5V) and a second (upper) horizontal arrow corresponding to a 660 mV rise (i.e., representing a 66% increase in output voltage), for which the corresponding difference in time may be calculated to determine the rise time.

In certain embodiments, electrodes used to perform measurements may be placed in contact with a comparatively large volume of a bulk suspension contained in a reservoir. In certain embodiments, electrodes used to perform measurements are placed in contact with a measurement channel (e.g., a fluidic channel, such as a microchannel) containing a smaller volume of a suspension. In such an embodiment, a first portion of a bulk suspension may be collected from a reservoir and placed into the measurement channel for analysis. After analysis, a second portion of the bulk suspension may be transferred into the measurement channel to replace the previously analyzed first portion. Subsequent portions may be transferred into the measurement channel and analyzed. In this manner, a large portion of the bulk suspension may be sampled over time to improve statistical analysis. Transfer of portions of a bulk suspension from a reservoir to a microchannel may be performed manually or automatically. In certain embodiments, a bulk suspension may be flowed through a measurement channel on an intermittent or substantially continuous basis to permit measurements to be performed at various time points. In certain embodiments, a bulk suspension may be circulated (e.g., pumped) and/or agitated within a reservoir and/or a measurement channel.

Various experiments have been performed utilizing a measurement channel having a square cross section of about 1 mm×1 mm, a length of about 4 cm, and a distance of about 1 cm between electrodes. However, it is to be appreciated that measurement channels of other shapes (e.g., channels of different cross sectional shapes, curved channels, and/or non-straight channels) and sizes (either larger or smaller than the preceding dimensions), as well as different electrode spacing, could be used. A measurement channel may be used in conjunction with a fluidic interface (e.g., for transfer and/or circulation of a suspension), an electrical interface (e.g., for transmission of electrical pulses and reception of signals indicative of electrical response upon application of electrical pulses), various signal processing and/or signal analyzing components, and a user interface.

FIG. 7 is a block diagram of components of a time domain impedance detection (TDID) system 30 according to one embodiment of the present disclosure. The TDID system 30 includes a channel 32 (which may be microfluidic in scale) and serves as a measurement channel, an electrical interface 34 coupleable to electrodes in electrical communication (e.g., conductive contact) with contents of the channel 32, and an instrument 36 associated with both the channel 32 and a user interface 46. The instrument 36 includes a mechanical system 42 that is coupleable with the channel 32 for fluid movement and/or mixing of a suspension. The instrument 36 additionally includes a signal generator 38 suitable for generating one or more DC pulses and coupleable to at least two electrodes associated with the channel 32. The instrument 36 further includes a signal analyzer 40 suitable to analyze signals received from at least two electrodes associated with the channel 32, such as to measure changes over time in microorganism charge and liquid media properties. At least one data analysis element 44 is further provided to process data received from the signal analyzer 40, such as to extract specific parameters that represent property changes in the liquid media. The user interface 46 may be used to input selective experimental parameters and display output signals.

In certain embodiments, the electrical interface 34 includes various electrical connections which can be used to connect the TDID system 30 to electrodes of the channel 32. These electrical connections can serve to convey input and output signals between electrodes and other components of the TDID system 30. In certain embodiments, the electrical interface 34 allows connection and disconnection of measurement channel electrodes and components of the instrument 36 associated with the TDID system 30. In certain embodiments, the electrical interface 34 may include cables of any suitable length (e.g., a few inches, 0.5 ft, 1 ft, 3 ft, or longer). To permit connection to electrodes associated with the channel 32, in certain embodiments, one or more ends of cables may be terminated with bayonet connectors, mini grabber connectors, alligator clips, slip connections with circuit boards, or any of various other conventional connectors. In certain embodiments, electrical connections may be made between a cartridge device and measurement instrumentation utilizing a compression connection. In certain embodiments, electrical cables may include shielding to reduce reception of external frequency noise. In certain embodiments, co-axial cables can be used to promote reduced noise. In certain embodiments, active and/or passive shielding (such as the use of a Faraday cage or other methods) may be used in conjunction with cables and/or connectors of a TDID system 30 as disclosed herein.

In certain embodiments, a rapid DC pulse may be applied to electrodes associated with the channel 32 (e.g., as an input signal), and such electrodes may be used to measure voltage and/or amperometric response of the TDID system 30 (e.g., as an output signal) following a change in state of the pulse. In certain embodiments, the TDID system 30 may include the signal generator 38 to apply a pulsed input signal, and may include the signal analyzer 40 to analyze the corresponding output signal. In certain embodiments, pulsed current/voltage signals may be applied at various frequencies and voltages using the signal generator 38, which may be connected to electrodes associated with the channel 32 using the electrical interface 34. For example, the pulse frequency could be 100 Hz, 10 KHz, 2 MHz, or any desired value within (or outside) the foregoing ranges. Similarly, applied voltage may vary, with exemplary values of voltage pulses supplied to electrodes being in a range of from 100 mV to 10V. As will be appreciated by one of ordinary skill in the art, wide ranges of pulse frequencies and applied voltages are possible. The signal analyzer 40 can measure changes in media suspension properties through electrical interaction between the electrodes associated with the channel 32.

In certain embodiments, the signal generator 38 may be used to supply a constant current signal in a pulse format to electrodes of the channel 32, and the corresponding voltage can be measured and tracked (e.g., via the signal analyzer 40) to determine microorganism (e.g., pathogen) growth.

Measurement channels (such as the channel 32) may be provided within fluidic devices that can be designed and fabricated in various ways. For example, fluidic devices containing one or more channels and configured to receive multiple electrodes may be three-dimensionally designed in various software programs (e.g., SOLIDWORKS® software (Dassault Systèmes SE, Vélizy-Villacoublay, France), PTC CREO® software (Parametric Technology Corporation, Needham, Mass., US), AUTOCAD® software (Autodesk, Inc., San Rafael, Calif., US), or the like). Additive and/or subtractive manufacturing processes may be used. Fluidic devices can be fabricated through 3D printing, injection molding, stacking and compression or adhesion of stencil layers (definable through various materials via laser ablation, blade cutting, or the like), photolithographic features definition followed by etching, or other methods, as would be recognized by one skilled in the art. Channel-containing fluidic devices may be printed with different types of non-conducting materials. One such example is photocurable polymeric resin, although other materials may be used.

In certain embodiments, measurement channels may embody trenches formed as recesses or grooves defined in at least one surface of a fluidic device, and may optionally be open on top. In certain embodiments, measurement channels may be formed of tubes of various shapes and dimensions, optionally including one or more tubing sections embedded or otherwise affixed in a body structure.

In certain embodiments, measurement channels may include width×depth×length dimensions of about 1 mm×1 mm×10 mm, or 0.3 mm×0.3 mm×5 mm, between electrodes. In certain embodiments, an entire measurement channel may be less than or equal to about 4 cm in length. In other embodiments, measurement channels exceeding 4 cm in length may be used. In certain embodiments, length:width and/or length:height aspect ratios for measurement channels could be 1:1, 2:1, 1:2, 3:1, 5:1, 7.5:1, 10:1, or other values. As would be readily understood by one of ordinary skill in the art, other channel shapes and dimensions are possible, other than the specific channel shapes and dimensions illustrated and/or discussed herein.

With continued reference to FIG. 7, in certain embodiments, the signal generator 38 and the signal analyzer 40 may be embodied in a function generator and an oscilloscope, respectively. In such an embodiment, wherein the signal generator 38 (e.g., function generator) may provide a pulsed input signal, and the signal analyzer 40 (e.g., oscilloscope) may be used to perform time domain voltage measurements. Voltage drop across a suspension between electrodes of the channel 32 may be measured. In certain embodiments, the signal generator 38 may provide a pulsed voltage signal at a specific frequency, and the signal analyzer 40 may serve to measure current transmitted between electrodes associated with the channel 32. In certain embodiments, an analog to digital (ND) converter could be used as part of the signal analyzer 40. In certain embodiments, functions of the signal generator 38 and the signal analyzer 40 may be performed by components (e.g., signal processors, signal converters, comparators, integrators, memory elements, and/or other components) associated with a single circuit board or a single controller.

As will be recognized by one of ordinary skill in the art, other automated (e.g., electronic) methods of applying an electrical signal to a sample and analyzing the corresponding electrical response may be utilized. In various examples described herein, a voltage (e.g., a voltage pulse signal) is applied to the system. However, as will be recognized by one of ordinary skill in the art, in other embodiments, a current (e.g., a current pulse signal) could be applied to a sample. Using the electrical measurement systems in the examples described herein, an output voltage system is recorded. However, in certain embodiments, an output current measurement may be recorded and analyzed.

In various embodiments, output signals received from electrodes associated with a measurement channel can be analyzed by curve-fitting, determining area under a curve, calculating of rise time, etc. In certain embodiments, curve-fitting can be performed by fitting a circuit equation to measured data and obtaining individual parameters of the equation. One such parameter can be an exponential rise in the square pulse. In certain embodiments, area under a curve can be determined by using mathematical calculations based on fitted parameters. In certain embodiments, rise time may be determined by calculating the time taken for a signal received from measurement channel electrodes to rise from a pre-specified change in state (e.g., initiation or termination of a voltage pulse). In certain embodiments, a process of data generation and analysis is repeated over a specified time period to determine the presence or absence of viable microorganisms (e.g., pathogens) in a bulk suspension.

With further reference to FIG. 7, the user interface 46 for the TDID system 30 according to certain embodiments may include a personal computer, laptop, embedded circuit, voltage counter, and/or any other type of processing device, preferably including a microprocessor configured to operate a machine-readable instruction set. In certain embodiments, the user interface 46 may include a display for viewing data as well as an input device to facilitate data entry and analysis. The user interface 46 may allow a user to enter experimental information and data, such as type of media, time of collection, time of recording, etc. In certain embodiments, the user interface 46 may be used to trigger the signal analyzer 40 to measure output electrical signals. In certain embodiments, the user interface 46 may be configured to automatically trigger and record measurements at pre-determined time intervals. In certain embodiments, the TDID system 30 may include embedded algorithms and may be configured to send results (e.g., positive/negative determinations, supporting data, etc.) via the user interface 46 or a dedicated communication element (not shown) directly to a laboratory information system.

Various non-limiting examples of fluidic devices including measurement channels and electrodes that are useable with embodiments disclosed herein are shown in FIGS. 8A-8E.

FIG. 8A is a schematic perspective view of a fluidic device 50 including a fluidic channel 54 with channel extensions 54A, 54B protruding through sidewalls of a body structure 52 and including two cylindrical electrodes 56A, 56B arranged perpendicular to the fluidic channel 54, according to one embodiment. As shown, a centerline of each electrode 56A, 56B intersects a centerline 53 of the fluidic channel 54. In use of the fluidic device 50, a suspension containing liquid media and microorganisms may flow through the fluidic channel 54 and contact the electrodes 56A, 56B. One or more electrical pulses may be applied to the electrodes 56A, 56B, and the same electrodes 56A, 56B may be used to detect electrical response of the fluidic device 50 and/or contents of the fluidic channel 54. For example, electrical response to an electrical pulse in a short initial time window (e.g., within 200 nanoseconds after a change in state of the electrical pulse) permits bulk electrical response of the suspension between the electrodes 56A, 56B to be determined before electrical response signals are dominated by double layer formation at surfaces of the electrodes 56A, 56B, whereas electrical response in an extended time window (e.g., no longer than about 20 microseconds after a change in state of the electrical pulse) may be used to normalize an initial electrical response signal.

FIG. 8B is a schematic perspective view of a fluidic device 60 including a fluidic channel 64 with channel extensions 64A, 64B protruding through a top wall of a body structure 62, and including two cylindrical electrodes 66A, 66B arranged perpendicular to the fluidic channel 64, with each electrode 66A, 66B being offset relative to a centerline 63 of the fluidic channel 64, according to one embodiment. Each channel extension 64A, 64B may include a fitting or port 65A, 65B for interfacing with an external fluidic interface optionally embodied in tubing, a manifold, or other fluid handling components. In a manner similar to the device 50 of FIG. 8A, one or more electrical pulses may be applied to the electrodes 66A, 66B, and the same electrodes 66A, 66B may be used to detect electrical response of the fluidic device 60 and/or contents of the fluidic channel 64.

FIG. 8C is a schematic perspective view of a fluidic device 70 including a fluidic channel 74 with channel extensions 74A, 74B protruding through a top wall of a body structure 72, and including two planar or plate-type electrodes 76A, 76B arranged above and below a central portion of the fluidic channel 74, respectively, according to one embodiment. In certain embodiments, the electrodes 76A, 76B may be arranged in non-contacting relationship with a suspension in the fluidic channel 74, with one or more wall materials and/or coatings arranged therebetween to preclude direct contact. In alternative embodiments, the electrodes 76A, 76B may be configured to contact fluid contents of the fluidic channel 74. Each electrode 76A, 76B is substantially parallel to a centerline 73 of the fluidic channel 74. Each channel extension 74A, 74B may include a fitting or port 75A, 75B for interfacing with an external fluidic interface (not shown) optionally embodied in tubing, a manifold, or other fluid handling components. In a manner similar to the fluidic devices 50, 60 of FIGS. 8A and 8B, one or more electrical pulses may be applied to the electrodes 76A, 76B, and the same electrodes 76A, 76B may be used to detect electrical response of the fluidic device 70 and/or contents of the fluidic channel 74. If the electrodes 76A, 76B are arranged in non-contacting relationship with a suspension within the fluidic channel 74, then a higher amplitude pulse (e.g., voltage or current pulse) may be required to transit through any intervening wall and/or coating material arranged between the electrodes 76A, 76B and the suspension, and/or response signals received by the electrodes 76A, 76B may be significantly attenuated, relative to utilization of alternative electrodes that may be configured to directly contact a suspension within the fluidic channel 74.

FIG. 8D is a schematic perspective view of a fluidic device 80 including a fluidic channel 84 with channel extensions 84A, 84B protruding through a top wall of a body structure 82, including a first electrode 86A arranged along an upper left boundary of the fluidic channel 84, and including a second electrode 86B arranged along a lower right boundary of the fluidic channel 84, according to one embodiment. The electrodes 86A, 86B may optionally include a greater length than width, with a length dimension being substantially parallel to a centerline 83 of the fluidic channel 84. Each channel extension 84A, 84B may include a fitting or port 85A, 85B for interfacing with an external fluidic interface (not shown) optionally embodied in tubing, a manifold, or other fluid handling components. In a manner similar to the fluidic devices 50, 60, 70 of FIGS. 8A-8C one or more electrical pulses may be applied to the electrodes 86A, 86B, and the same electrodes 86A, 86B may be used to detect electrical response of the fluidic device 80 and/or contents of the fluidic channel 84.

FIG. 8E is a schematic perspective view of a fluidic device 90 including a fluidic channel 94 with channel extensions 94A, 94B protruding through a top wall of a body structure 92, and including two pairs of cylindrical electrodes (e.g., an outer pair of electrodes 96A, 96B, and an inner pair of electrodes 97A, 97B) arranged perpendicular to the fluidic channel 94, with each electrode 96A, 96B, 97A, 97B being offset laterally relative to a centerline 93 of the fluidic channel 94, according to one embodiment. In certain embodiments, the outer pair of electrodes 96A, 96B may be used to apply electrical pulses to contents of the fluidic channel 94, and the inner pair of electrodes 97A, 97B may be used to detect electrical response of the fluidic device 90 and/or contents of the fluidic channel 94. Each channel extension 94A, 94B may include a fitting or port 95A, 95B for interfacing with an external fluidic interface (not shown) optionally embodied in tubing, a manifold, or other fluid handling components.

Various non-limiting examples of cross-sectional shapes of measurement channels that are useable with embodiments disclosed herein are shown in FIGS. 9A-9C. FIG. 9A is a schematic cross-sectional view of a portion of a fluidic device 100 including a body structure 102 defining a fluidic channel 104 having a square-like cross-sectional shape, according to one embodiment. FIG. 9B is a schematic cross-sectional view of a portion of a fluidic device 110 including a body structure 112 defining a fluidic channel 114 having a round cross-sectional shape, according to one embodiment. FIG. 9C is a schematic cross-sectional view of a portion of a fluidic device 120 including a body structure 122 defining a fluidic channel 124 having a narrow rectangular cross-sectional shape, according to one embodiment. Although the body structures 102, 112, 122 shown in FIGS. 9A-9C each include cross-sections with rectangular shapes, it is to be appreciated that body structures having other cross-sectional shapes (e.g., annular, oval, polygonal, etc.) may be used.

FIG. 10 is a schematic perspective view of a fluidic device 60 according to FIG. 8B with electrodes 66A, 66B thereof being connected to electrical contacts 69A, 69B of a TDID system according to one embodiment, wherein the electrical contacts 69A, 69B may be embodied in an electrical interface of an instrument as described previously herein. Other elements of the fluidic device 60 remain the same as described previously herein in connection with FIG. 8B.

As will be recognized by one of ordinary skill in the art, electrodes of various materials, shapes, sizes, conformations, and placement may be used. As depicted in FIGS. 8A-8E, electrodes may be placed in or along a fluidic channel in various conformations, such as offset along the length and/or width, centered along the length and/or width, or aligned against the walls of the channel. In certain embodiments, planar electrodes may be provided, and may be designed to be in contact with, or not to be in contact with, a suspension to be contained within a fluidic channel.

Different types of electrodes that can potentially be used with measurement channels of fluidic devices disclosed herein include solid gold electrodes, gold-coated electrodes, copper electrodes, platinum electrodes, silver electrodes, chemically modified electrodes, surface modified electrodes, and conductive electrodes. In certain embodiments, one or more portions of electrodes may be coated with one or more limited- or reduced-conductivity materials to limit or minimize electrical current that may pass through a suspension within a measurement channel during measurement steps. Length and width or diameter of electrodes may be varied. In certain embodiments, one or more portions of an electrode may have a width or diameter of 0.5 mm, 1 mm, 2 mm, 3 mm, or another suitable size. In certain embodiments, one or more portions of an electrode can be cylindrical, circular, rectangular, square, arc-shaped, or planar. In certain embodiments, electrodes may be arranged to directly contact contents (e.g., a suspension) of a measurement channel of a fluidic device. In other embodiments, electrodes (e.g., planar electrodes) may be arranged in non-contacting relationship with a suspension contained in a measurement channel of a fluidic device. When planar or plate-like electrodes are used, in certain embodiments such electrodes may comprise one or more conductive materials, such as aluminum foil or copper sheets. In certain embodiments, planar electrodes may be constructed using circuit board technology with photolithographic patterning followed by selective etching being useable to define shapes of the electrodes. In certain embodiments, planar electrodes may be fabricated with photolithographic patterning followed by selective deposition or selective etching to result in formation of electrodes on substrates such as glass, silicon, or other materials. The shape and dimensions of substrates and electrodes may vary depending on the application. Electrodes may have either rough or smooth surfaces.

In certain embodiments, electrodes may be cleaned with various chemicals (e.g., ethanol, acetone, and/or water) and/or detergents before usage of a fluidic device. Various reagents and/or detergents may be used. In certain embodiments, it may be unnecessary to clean electrodes of a fluidic device prior to use of the device for methods disclosed herein.

In certain embodiments, various fluidic devices described herein may be cleaned thoroughly with ethanol and acetone (and/or other suitable agents) prior to use. In certain embodiments, fluidic devices may be cleaned prior to use with autoclaving, plasma ion cleaning, or other standard cleaning technologies. Alternatively, if fluidic devices are produced under sterile conditions and/or are pre-sterilized, then no cleaning may be necessary. In certain embodiments, fluidic devices disclosed herein can additionally or alternatively be cleaned by soaking overnight in a mixture of soap and warm water. Different combinations of chemicals and/or detergents can be used to clean the devices before usage. The foregoing cleaning steps may be eliminated in certain embodiments. Separately, one or more surfaces intended to be wetted with a suspension (e.g., measurement channel surfaces) may be treated with one or more materials to enhance sensitivity, to improve fluid mobility, and/or alter the overall hydrophobic/hydrophilic nature of the surfaces.

Various examples described herein include electrodes that are in fluid communication with a suspension to be analyzed. As will be recognized by one of ordinary skill in the art, electrodes need not be in fluid communication with a sample in order to induce the electrical response described by the present disclosure. In certain embodiments, electrodes may be coated with an insulating material or coating in order to avoid direct connection between conductive surfaces of an electrode and a sample to be analyzed. In certain embodiments, electrodes may be arranged outside boundaries of, but in close physical proximity to, a measurement channel containing a sample to be analyzed. In such cases, characteristics and/or values of signals produced by electrodes arranged in a non-contacting relationship with a sample to be analyzed may be attenuated or otherwise altered relative to application of a comparable electrical signal to electrodes arranged in contact with the suspension. The electrical signal applied to the system and corresponding electrical response signal will be different than signals where the electrodes are in fluid communication with the system. However, as will be recognized by one of ordinary skill in the art, the resulting signals can be analyzed utilizing the methodology described herein to determine the presence of pathogenic material in the sample. Electrical input signals applied to such a system may be adjusted to optimize (e.g., increase signal-to-noise ratio of) the corresponding electrical output signal to facilitate analysis.

FIG. 11A is a schematic diagram showing electrical connections and fluidic connections of a TDID system 130 according to one embodiment, with the TDID system 130 including a fluidic device 50 according to FIG. 8A. The TDID system 130 includes a mechanical subsystem 132 and an electrical subsystem 140. The fluidic device 50 includes a fluidic channel 54 (i.e., a measurement channel) with channel extensions 54A, 54B extending through a body structure 52, and includes two electrodes 56A, 56B in electrical communication with the fluidic channel 54. Within the mechanical subsystem 132, the channel extensions 54A, 54B of the fluidic device 50 are coupled with a fluidic circuit including a reservoir 134 and a pump 136 configured to automatically supply portions of a bulk suspension from the reservoir 134 into the fluidic channel 54 to contact the electrodes 56A, 56B. The electrical subsystem 140 includes control circuitry 142 arranged to provide signals to a signal generator 144, and arranged to receive signals from a signal analyzer 146. The control circuitry 142 may also be coupled with a communication module 148, which may be coupled to a user interface (not shown) and/or a laboratory information system (not shown). Although a pump 136 is shown, it is to be appreciated that any suitable fluid transfer device could be used to supply a bulk suspension to a fluidic channel 54, such as a pressure and/or vacuum source, a gravitational flow apparatus, a pipettor device, or the like.

The control circuitry 142 may include a central processing unit (CPU) and memory to enable the control circuitry 142 to directionally or bi-directionally communicate with the communication module 148 or other devices over a communication bus or another appropriate communication interface. The control circuitry 142 may communicate output information and/or receive user inputs and/or instructions from the communication module 148. In certain embodiments, the signal analyzer 146 may include a digital signal processing module.

In certain embodiments, the control circuitry 142 may be used to control operation of the signal generator 144 to apply one or more DC pulse signals to the electrodes 56A, 56B of the fluidic device 50. In certain embodiments, the signal analyzer 146 is configured to receive signals from the electrodes 56A, 56B to determine electrical response of the suspension between the electrodes 56A, 56B during a short initial time period following a change in state of a pulse signal, and to determine electrical response of the suspension plus the electrodes 56A, 56B during an extended time period following a change in state of a pulse signal.

FIG. 11B is a schematic block diagram showing stages internal to the signal analyzer 146 of the electrical components of the TDID system 130 depicted in FIG. 11A. In certain embodiments, the signal analyzer 146 may include an amplitude detector stage 150, a differentiator stage 152, and a logic (or comparator) stage 154. An exemplary amplitude detector stage 150 may detect amplitude of a received voltage or current signal. The differentiator stage 152 may include a differentiator to determine a change in a received signal with respect to time. The logic (or comparator) stage 154 may compare a received signal with one or more threshold signals (e.g., a predetermined voltage or current threshold). An exemplary logic (or comparator) stage 154 may include a comparator and an integrator. The integrator of the logic (or comparator) stage 154 may be used to integrate a digital signal of the comparator and generate an output signal of the signal analyzer 146 that may be provided to the control circuitry 142. Although FIG. 11A discloses circuitry according to one implementation, it is to be appreciated that other circuits for supplying pulse signals and detecting received response signals may be used with fluidic devices as disclosed herein.

Various methods may be used to introduce portions of a suspension (i.e., a sample) into a measurement channel. In certain embodiments, portions of a suspension may be transferred from a reservoir to a measurement channel via fixed-volume manual pipetting, with removal of a previously transferred volume from a measurement channel between sample insertions. A measurement channel could also be flushed with fresh solution between readings. In certain embodiments, disposable closed containment devices containing media suspensions and measurement channels may receive portions of a fluidic suspension from a reservoir through a mechanical system including components such as a peristaltic pump or the like. In certain embodiments, when a suspension is inserted into a measurement channel, the suspension may surround and contact terminal portions of electrodes. The volume of the suspension in a measurement channel and present between electrodes associated with the channel may be dictated by dimensions of the measurement channel.

In certain embodiments, a measurement channel with associated electrodes may be constructed in a body structure incorporating a reservoir embodied in a sample incubation bottle, and no manual intervention is required to introduce portions of a bulk suspension from the reservoir into the measurement channel. Automatic introduction of a suspension into a measurement channel may be accomplished in various ways, as will be appreciated by one of ordinary skill in the art. As one example, passive mixing through a periodic rocking motion (e.g., using a solenoid- or motor-driven rocking apparatus) could be used to cause portions of a bulk suspension to move in and out of a measurement channel. As another example, peristaltic pumping could be used to move portions of a bulk suspension in and out of a measurement channel. Other automated methods for introducing portions of a sample into a measurement channel could be employed.

In certain embodiments, a channel or chamber in which pathogens are grown or incubated embodies the same channel or chamber in which electrical measurements are conducted. For example, a sample to be analyzed may be placed into a measurement channel and monitored over time without removal of the sample from the measurement channel (optionally, further without introduction of additional fluids into the measurement channel).

FIG. 12A illustrates an assembly 200 incorporating a reservoir 204, a sample analysis segment 215 including electrodes 216A, 216B contacting a measurement channel 214, first and second channel extension segments 214A, 214B, and a pump interface region 222 integrated into a body structure 202. The measurement channel 214 includes a length of about 5 mm and a diameter of 1 mm. The reservoir 204 includes a horizontally arranged generally cylindrical body that is supported by support leg portions 212 and a base portion 210 of the body structure 202. An upper neck 206 and a lid 208 allow introduction of a bulk suspension and optional growth media into the reservoir 204. The first channel extension segment 214A is configured to enable a portion of the bulk suspension to be withdrawn using an automatic rotary squeeze-type pump (shown in FIG. 12B) that is receivable by the pump interface region 222. The pump interface region 222 includes a curved section of flexible tubing 220 mounted between fittings 218A, 218B and proximate to a rigid curved surface 223 of the body structure 202, whereby periodic clockwise rotary motion of spaced rollers of the squeeze-type pump compressed against the flexible tubing 220 causes plugs of bulk suspension within the flexible tubing 220 to be transported upward into the measurement channel 214 of the sample analysis segment 215, where it is placed in contact with the electrodes 216A, 216B. Following change in state of a pulsed signal to the electrodes 216A, 216B, the bulk suspension exhibits an initial electrical response (and the bulk suspension in combination with the electrodes 216A, 216B exhibits an extended electrical response) that is detectable with the electrodes 216A, 216B and subject to analysis. Thereafter, the portion of the bulk suspension within the measurement channel 214 may be returned via the second channel extension 214B to the reservoir 204. Operation of a pump associated with the assembly 200 may therefore transport bulk suspension from the reservoir 204 to the measurement channel 214 in an automated manner without requiring manual fluid transport and/or actuation.

FIG. 12B is a side cross-sectional view of a portion of a rotary squeeze pump 225 suitable for cooperating with the pump interface region 222 and flexible tubing 220 of the assembly 200 of FIG. 12A. The rotary squeeze pump 225 may be driven by a drive source such as a motor (not shown). The flexible tubing 220 is disposed along an inner circumference of the rigid curved surface 223. First and second opposing pressing rollers 230, 231 are rotated on a center of an axis 228 in a direction indicated by the arrow, while pressing portions of the flexible tubing 220 against the inner circumference of the rigid curved surface 223. Such motion causes a first aliquot of bulk suspension within a first segment 221A of the flexible tubing 220 to be transported upward ahead of the first pressing roller 230, while a second aliquot of bulk suspension within a second segment 221B of the flexible tubing 220 is transported ahead of the second pressing roller 231.

In an initial experiment supporting the present disclosure, the inventors did not use a function generator to applied said voltages. Instead, a single pulse was applied to electrodes of a measurement channel using custom electronics, and the response from such pulse was monitored. Application and measurement of the single pulse was periodically repeated over time to determine changes in properties of a bulk suspension.

Notable examples of bacterial growth tests using systems and methods according to the present disclosure are described below.

Example 1

3D designs of fluidic devices including fluidic channels, according to FIG. 8B, were made using SOLIDWORKS® software, and were fabricated via 3D printing using an Eden 350/350B printer. The 3D printed fluidic devices were made with veroclear-rgea10, which is a non-conducting, transparent, rigid, and nearly colorless material. These cassettes contained trench channels with dimensions of 1 mm height, 1 mm width, and 10 mm length, with the length dimension extending between electrodes. Each 3D printed fluidic device was cleaned thoroughly by scrubbing with soap and warm water. After drying, each fluidic device was sealed to a glass microscope slide via a double-sided, medical grade adhesive (~10 microns thick) to form a closed measurement channel. Before usage, the glass slide was cleaned with acetone, ethanol, and water, respectively.

1 mm diameter gold-coated electrodes were cleaned with acetone, ethanol, and water before insertion of two electrodes into each measurement channel. Electrical connectors from electrodes to a TDID system according to FIG. 10 were made at the start of the experiment and remained connected for the duration of the experiment. In this case, the electrical interface included BNC-mini grabber cables having lengths of about 2 feet.

Time domain impedance measurements were taken at each time point (every 30 minutes) for each aliquot of the sample suspension.

*Escherichia coli* (ATCC 25922) and *Klebsiella pneumoniae* (ATCC 700603) were used in this study. In order to produce load cultures of bacteria, both *E. coli* and *K. pneumoniae* were incubated overnight for 10-14 hours at 37° C. in Tryptic Soy Broth (TSB) (RPI Corp.). The suspensions were spun down for 10 min and re-suspended twice in fresh sterile TSB. The optical density of the re-suspended samples was adjusted to obtain a concentration of ~$10^8$ CFU/ml. The suspensions were then serially diluted to a concentration of ~$10^2$ CFU/ml. The appropriate dilution was added to 30 ml of freshly made, sterile TSB to give initial loads of 2 CFU/ml and 40 CFU/ml for *E. coli* and 70 CFU/ml for *K. pneumoniae*. A control containing only TSB (without microorganisms) was also used in this study. The control was not contaminated during the course of the experiment, which was verified by plating at each time point (i.e., every 30 mins.). The suspensions—namely, both microorganism-containing samples and the controls—were then incubated at 37° C. for 30 minutes before initial readings were taken.

At the time of the initial reading (0 hr), 100 µl aliquots of the suspensions were plated onto Tryptic Soy Agar (TSA) plates and placed in an incubator at 37° C. Simultaneously, 400 µl of each suspension was extracted, and the sample and the suspensions were placed back in the incubator at 37° C. Each suspension was manually injected into a separate measurement channel in 3 separate aliquots. Each aliquot was 100 µl of the suspension, while another 100 µl of the suspension was used before the first aliquot to flush any previously injected liquid suspension out of the measurement channel of the respective fluidic device.

Time domain impedance measurements using the TDID system as disclosed herein were taken by applying electrical square pulses having a frequency of 10 KHz and a voltage of 1V (peak-to-peak) to the electrodes. The same electrodes were used to detect the electrical response. This process was repeated every 30 min for a period of 8 hrs, with the appropriate dilutions for plating.

Data generation and analysis was repeated for the 8 hr period to determine the presence of pathogens. The data was analyzed by curve-fitting and rise time. For the curve-fitting analysis, the time domain impedance data was fitted to a mathematical expression as follows:

$$y = a + b(1 - e^{-cx})$$

where y is the output voltage, x is time, a is the initial voltage value (intercept), b is the amplitude of the pulse, and c is the exponential component of the curve. An increase in parameter C from the baseline indicated the presence of pathogens in the sample composition. Thus, the lack of a steady increase in parameter C indicates the lack of pathogen growth. The percentage change for parameter C was determined to be ~6.0% for the *E. coli* sample with ~2 CFU/ml initial load, ~3.0% for the *E. coli* sample with ~40 CFU/ml initial load, and ~5.0% for the *K. pneumoniae* sample with ~70 CFU/ml initial load. Over time, the percentage change for parameter C fluctuated between ~±1.0% for the control (TSB only). FIG. 13 is a graph of the percentage change of parameter C versus time for the ~2 CFU/ml initial load *E. coli* sample. FIG. 14 is a graph of parameter C versus time for the ~70 CFU/ml initial load *K. pneumoniae*. FIG. 15 is a graph of parameter C versus time for the ~40 CFU/ml initial load *E. coli* and control (TSB only). Data analysis also included the calculation of rise time. The rise time is the amount of time necessary for an output voltage to rise to a pre-specified voltage, which in this case was 0.63V (63% of the steady state voltage). The rise time and pathogen (microorganism) count have an inverse relationship, so that as pathogens proliferate, the rise time decreases. FIG. 16 is a plot of time constant (µs) versus time (hrs) for an 8 hr experiment utilizing a TDID system as disclosed herein with an initial load of 70 CFU/ml of *K. pneumoniae* (ATCC 700603) in TSB. In this particular case, the rise time decreased by ~5.0% for the *K. pneumoniae* sample with ~70 CFU/ml initial load, as represented by FIG. 16.

Example 2

A disposable closed-containment assembly 200 according to FIG. 12A containing a measurement channel with a 1 mm diameter and a distance of 5 mm between electrodes was designed and 3D printed using non-conducting resins (with the device being referred to in the remainder of this example as a bottle). The maximum fluid holding capacity of the reservoir of the bottle was 90 ml.

Gold-coated electrodes with a diameter of 1 mm were inserted into a measurement channel configured to receive a portion of liquid from the bottle. The electrodes were offset on opposite sides of the width of the channel.

The bottle was inserted into a station that is part of a mechanical system. The mechanical system consisted of multiple stations (each of which could be shaken individually or collectively) and also included a fluid pumping mechanism to facilitate fluid movement in the reservoir of the bottle. The settings for the mechanical system could be switched to shake softly or vigorously.

One end of the bottle contained flexible tubing that allowed for peristaltic pumping of the fluid into the measurement channel. Prior to each reading, the peristaltic pump came into contact with the bottle's tubing in order to pump fresh fluid into the channel for a specified amount of time.

An electrical interface contained a circuit board, which was pre-programmed to provide the necessary input voltage signal to electrodes associated with the measurement channel, and to read the processed output voltage signal. The circuit board was connected to the bottle using a slip-connection. Before each reading, the peristaltic pump and the circuit board were configured to move to and come in contact with the appropriate bottle.

*E. coli* (ATCC 25922) was used in this experiment. A subculture was incubated overnight for 10-14 hours at 37° C. in TSB (RPI Corp.). 1 ml of the subculture suspension was spun down for 10 min and re-suspended twice in fresh sterile TSB. The optical density was adjusted to obtain a concentration of ~$10^8$ CFU/ml. The suspension was serially diluted and plated on TSA plates to obtain actual colony counts. The appropriate dilution was added to 30 ml of fresh sterile TSB to give an initial load of ~10000 CFU/ml. The mixture was then added to the reservoir of a bottle for measurements.

The bottle was inserted into the mechanical system and allowed to shake for 30 min before the first reading. The system was automated to take measurements at a specific time interval for a period of 6 hrs. Therefore, over the remaining course of the experiment, sample handling was automated without any manual intervention.

The data was analyzed by curve-fitting to the above-mentioned equation, namely:

$$y=a+b(1-e^{-cx})$$

where y is the output voltage, x is the time, a is the initial voltage value (intercept), b is the amplitude of the pulse, and c is the exponential component of the curve. In this particular case, an increase in parameter C from the baseline during the course of the experiment indicated the presence of pathogens in the sample composition. The percentage change for parameter C was determined to be ~3.0% over the 6 hr experiment. FIG. 17 is a graph of parameter C versus time.

Example 3

Fluidic devices were made in the same manner as described above in Example 1. Each fluidic device contained fluidic trench channels with height×width×length (between the two electrodes) dimensions of 1 mm×1 mm×50 mm. The electrodes were offset along the width of the measurement channel. Each 3D printed fluidic device was cleaned thoroughly by scrubbing with soap and warm water. After drying, each fluidic device was sealed to a glass microscope slide via a medical grade adhesive to form a closed measurement channel. Before usage, the glass microscope slide was cleaned with soap and water.

1 mm diameter gold-coated cylindrical electrodes were used. Electrical connections from electrodes to a TDID system according to FIG. 10 were made at the start of the experiment and remained connected for the duration of the experiment. The electrical interface included BNC-mini grabber cables having lengths of about 2 feet.

*Klebsiella pneumoniae* (ATCC 700603) was the pathogenic microorganism used in this study. In order to produce load cultures of bacteria, *K. pneumoniae* was incubated overnight for 10-14 hours at 37° C. in Tryptic Soy Broth (TSB) (RPI Corp.). In the morning, a subculture was allowed to incubate at 37° C. in TSB for 3 hrs. The subculture was assumed to have a concentration of ~$10^8$ CFU/ml. The subculture was then serially diluted until a concentration of ~$10^4$ CFU/ml was obtained.

3 aliquots of each concentration ($10^4$, $10^5$, $10^6$, $10^7$, and $10^8$ CFU/ml) resulting from the serial dilution were manually injected into a measurement channel. Each aliquot included 150 µl of the desired concentration of the suspension.

Time domain impedance measurements using the TDID system as disclosed herein were taken by applying an electrical square pulse having a frequency of 10 KHz and a voltage of 1V (peak-to-peak) to the electrodes. The electrodes then detected the electrical response. This process was repeated for each concentration.

Data generation and analysis was repeated for the serial dilution to determine the presence of pathogens. The data was analyzed by curve-fitting. For the curve-fitting analysis, the time domain impedance data was fitted to a mathematical expression as follows:

$$y=(a/\pi)[\arctan((x-b)/c)+(\pi/2)]$$

where y is the output voltage, x is time, a is the initial voltage value (intercept), b is the transition height, c is the transition center, and d is the transition width. Decreases in parameters b and d from the initial concentration indicate an increase in concentration of pathogens (bacteria) in the sample compositions.

FIG. 18 is a plot of parameter b (in volts) versus concentration of bacteria for analysis of the 3 aliquots of each concentration ($10^4$, $10^5$, $10^6$, $10^7$, and $10^8$ CFU/ml), showing a linear decrease in parameter b with rising bacterial concentration.

FIG. 19 is a plot of parameter d (in microseconds) versus concentration of bacteria for the 3 aliquots of each concentration ($10^4$, $10^5$, $10^6$, $10^7$, and $10^8$ CFU/ml), showing a substantially curvilinear decrease in parameter d with rising bacterial concentration.

FIG. 20 is a plot of the product of parameter b and parameter d versus concentration of bacteria for the 3 aliquots (similarly showing a substantially curvilinear decrease in the product of the two parameters with rising bacterial concentration), while FIG. 21 is a graph of the quotient of parameter b and parameter d versus concentration of bacteria for the 3 aliquots (showing a substantially curvilinear increase in the quotient of the two parameters with rising bacterial concentration). As will be understood by one of ordinary skill in the art, various curve-fitting equations and parameters can be utilized for the detection of changes in the liquid media properties and pathogen charge storing properties across suspensions. In this example, the values for two different parameters were determined through curve-fitting data from one set of serial dilution suspensions. Both parameter b and parameter d are indicative of the increase in bacterial concentration across the serial dilution suspensions. Mathematical operations were performed on the two parameters to further analyze the data. The product and quotient of these two parameter values demonstrates that there is a directional trend for both values (decreasing values for the product; increasing values for the quotient) across bacterial concentration. These results demonstrate that the application of mathematical operations to multiple parameters can produce values that also indicate the presence of pathogens in the sample composition. Although a specific mathematical equation was used to extract these specific parameters for this experiment, depending on the biological system and its components, various other mathematical curve-fitting equations and parameters can be employed with methods described herein.

Separately from the preceding Examples, to illustrate the effects (if any) of system configuration differences (e.g., electrode spacing) and/or operational parameters (e.g., pathogen concentration and input voltage) on electrical response, various experiments were performed. Results of such experiments are tabulated in FIGS. 22-24.

FIG. 22 is a plot of voltage (V) versus time (µs) for the averaged rising edge output (response) signals responsive to the application of twenty 1V DC pulses for two different concentrations ($10^4$ CFU/ml and $10^8$ CFU/ml) of *E. coli* in TSB obtained by utilizing a TDID system according to one embodiment. Such figure shows differences in the two response signals above and below a voltage value of about zero volts, demonstrated by a lack of full overlap between the two plots.

FIG. 23 is plot of voltage (V) versus time (µs) for the averaged rising edge output (response) signals responsive to the application of twenty 1V DC pulses for TSB in four measurement channels with different distances between the two electrodes (0.5 cm, 1 cm, 2 cm, and 5 cm) obtained by utilizing a TDID system according to one embodiment. Such figure shows very significant differences in shapes of electrical response plots for different electrode spacing values— with smaller electrode spacing values facilitating a more rapid and more nearly exponential attainment of steady state electrical response, and with greater electrode spacing facilitating a much slower and more nearly linear attainment of steady state electrical response.

FIG. 24 is plot of voltage (V) versus time (µs) for the averaged rising edge output (response) signals responsive to the application of twenty DC pulses with three different applied voltages (500 mV, 1V, and 2V) obtained by utilizing a TDID system according to one embodiment. Such figure shows significant differences in shapes of electrical response plots for different applied voltages, with higher voltage values tending to correspond to slower attainment of steady state electrical response.

FIG. 22-24 thus demonstrate that a number of different system configuration differences and/or operational parameters (including but not limited to, bulk suspension properties (e.g., including pathogen charge storing properties), distance between electrodes, and applied voltage) can impact response signals. Changing the applied voltage for the DC pulse and/or the microorganism concentration in a suspension changes the slope of a response signal rising edge. Changing the distance between the at least two electrodes changes the slope of the response signal rising edge. The best mode of data analysis and normalization may vary depending upon the properties of the TDID system disclosed herein. It is to be understood that there are many other properties (e.g., system configuration differences and/or operational parameters) of TDID systems and methods disclosed herein that may alter the shape of a rising edge of an electrical response signal. Although not shown in FIGS. 22-24, it is to be appreciated that similar changes can also be observed on the falling edge of the response signal. As will be appreciated by one of ordinary skill in the art, any of various system configuration differences and/or operational parameters of a TDID system disclosed herein may be adjusted to optimize (e.g., increase signal-to-noise ratio of) the corresponding electrical output signal to facilitate analysis.

Those skilled in the art will recognize improvements and modifications to the preferred embodiments of the present disclosure. All such improvements and modifications are considered within the scope of the concepts disclosed herein and the claims that follow.

What is claimed is:

1. A method for detecting presence of at least one pathogen in a liquid-containing sample, the method comprising:
    applying a first electrical pulse between at least two electrodes in electrical communication with at least a portion of the liquid-containing sample;
    detecting a first initial electrical response of the at least a portion of the liquid-containing sample and the at least two electrodes due to application of the first electrical pulse, to generate at least one first initial electrical response signal that is indicative of an electrical response in a first initial time window that extends no longer than a time required to attain 95% of a steady state electrical response value after a change in state of the first electrical pulse;
    applying a second electrical pulse between the at least two electrodes in electrical communication with at least a portion of the liquid-containing sample;
    detecting a second initial electrical response of the at least a portion of the liquid-containing sample and the at least two electrodes due to application of the second electrical pulse, to generate at least one second initial electrical response signal that is indicative of an electrical response in a second initial time window that extends no longer than the time required to attain 95% of the steady state electrical response value after a change in state of the second electrical pulse; and
    comparing a second electrical response embodying or derived from the at least one second initial electrical response signal to a first electrical response embodying or derived from the at least one first initial electrical response signal.

2. The method of claim 1, wherein:
    the at least a portion of the liquid-containing sample to which the first electrical pulse is applied comprises a first portion of the liquid-containing sample;
    the at least a portion of the liquid-containing sample for which the first initial electrical response is detected comprises the first portion of the liquid-containing sample;
    the at least a portion of the liquid-containing sample to which the second electrical pulse is applied comprises a second portion of the liquid-containing sample; and
    the at least a portion of the liquid-containing sample for which the second initial electrical response is detected comprises the second portion of the liquid-containing sample.

3. The method of claim 2, wherein the at least two electrodes are in electrical communication with a fluidic channel, and the method further comprises:
    supplying the first portion of the liquid-containing sample to the fluidic channel prior to applying the first electrical pulse; and
    supplying the second portion of the liquid-containing sample to the fluidic channel prior to applying the second electrical pulse.

4. The method of claim 3, wherein the second portion of the liquid-containing sample is supplied to the fluidic channel more than about 10 minutes after the first portion of the liquid-containing sample is supplied to the fluidic channel.

5. The method of claim 2, further comprising:
    detecting a first extended electrical response of the first portion of the liquid-containing sample and the at least two electrodes due to application of the first electrical pulse, to generate at least one first extended electrical response signal that is indicative of an electrical response in a first extended time window that extends longer than the first initial time window by a factor of at least about 5 after the change in state of the first electrical pulse;
    detecting a second extended electrical response of the second portion of the liquid-containing sample and the at least two electrodes due to application of the second electrical pulse, to generate at least one second extended electrical response signal that is indicative of an electrical response in a second extended time window that extends longer than the second initial time window by a factor of at least about 5 after the change in state of the second electrical pulse; and
    utilizing the at least one first extended electrical response signal to normalize the at least one first initial electrical response signal to derive the first electrical response, and utilizing the at least one second extended electrical response signal to normalize the at least one second initial electrical response signal to derive the second electrical response.

6. The method of claim 1, wherein the at least a portion of the liquid-containing sample to which the first electrical pulse is applied comprises the same at least a portion of the liquid-containing sample to which the second electrical pulse is applied.

7. The method of claim 1, comprising at least one of the following features (i) or (ii): (i) the change in state of the first electrical pulse comprises a current rise or a voltage rise, or (ii) the change in state of the second electrical pulse comprises a current rise or a voltage rise.

8. The method of claim 1, comprising at least one of the following features (i) or (ii): (i) the change in state of the first electrical pulse comprises a current drop or a voltage drop, or (ii) the change in state of the second electrical pulse comprises a current drop or a voltage drop.

9. The method of claim 1, wherein the at least one first initial electrical response signal comprises a time value corresponding to attainment of a predetermined or user-determined voltage or current value.

10. The method of claim 1, wherein the at least one first initial electrical response signal comprises at least one curve fitting parameter derived from a plurality of measured electrical response values obtained in the first initial time window.

11. The method of claim 1, wherein the first initial time window extends no longer than about 100 nanoseconds after the change in state of the first electrical pulse, and the second initial time window extends no longer than about 100 nanoseconds after the change in state of the second electrical pulse.

12. The method of claim 1, wherein:
the at least two electrodes comprise a first pair of electrodes and a second pair of electrodes;
the applying of the first electrical pulse between the at least two electrodes comprises applying the first electrical pulse between the first pair of electrodes;
the applying of the second electrical pulse between the at least two electrodes comprises applying the second electrical pulse between the first pair of electrodes;
the detecting of the first initial electrical response comprises use of the second pair of electrodes; and
the detecting of the second initial electrical response comprises use of the second pair of electrodes.

13. A system for detecting presence of at least one pathogen in a liquid-containing sample, the system comprising:
a fluidic channel configured to receive the liquid-containing sample;
at least two electrodes in electrical communication with the fluidic channel;
control circuitry operationally coupled with pulse generator circuitry, signal detection circuitry, and comparison circuitry;
pulse generator circuitry operatively coupled with the at least two electrodes and the control circuitry is programmed to cause the pulse generator circuitry to generate a first electrical pulse across the at least two electrodes when the at least two electrodes are in electrical communication with at least a portion of the liquid-containing sample, and to generate a second electrical pulse across the at least two electrodes when the at least two electrodes are in electrical communication with at least a portion of the liquid-containing sample;

signal detection circuitry operatively coupled with the at least two electrodes and the control circuitry is programmed to cause the signal detection circuitry (i) to detect a first initial electrical response of the at least a portion of the liquid-containing sample due to application of the first electrical pulse to generate at least one first initial electrical response signal indicative of electrical response in a first initial time window extending no longer than a time required to attain 95% of a steady state electrical response value after a change in state of the first electrical pulse, and (ii) to detect a second initial electrical response of the at least a portion of the liquid-containing sample due to application of the second electrical pulse to generate at least one second initial electrical response signal indicative of electrical response in a second initial time window extending no longer than the time required to attain 95% of the steady state electrical response value after a change in state of the second electrical pulse; and
comparison circuitry operatively coupled with the signal detection circuitry and the control circuitry is programmed to cause the comparison circuitry to compare a second electrical response embodying or derived from the at least one second initial electrical response signal to a first electrical response embodying or derived from the at least one first initial electrical response signal.

14. The system of claim 13, wherein:
the at least a portion of the liquid-containing sample for which the first electrical pulse is generated comprises a first portion of the liquid-containing sample; the at least a portion of the liquid-containing sample for which the at least one first initial electrical response signal is generated comprises the first portion of the liquid-containing sample;
the at least a portion of the liquid-containing sample for which the second electrical pulse is generated comprises a second portion of the liquid-containing sample; and
the at least a portion of the liquid-containing sample for which the at least one second initial electrical response signal is generated comprises the second portion of the liquid-containing sample.

15. The system of claim 14, further comprising a reservoir configured to hold the liquid-containing sample, wherein the fluidic channel is configured to receive the first portion of the liquid-containing sample and the second portion of the liquid-containing sample from the reservoir.

16. The system of claim 15, further comprising a fluid transfer device configured to transfer the first portion and the second portion of the liquid-containing sample from the reservoir to the fluidic channel.

17. The system of claim 13, wherein the at least one first initial electrical response signal comprises a time value corresponding to attainment of a predetermined or user-determined voltage or current value.

18. The system of claim 13, wherein the at least one first initial electrical response signal comprises at least one curve fitting parameter derived from a plurality of measured electrical response values obtained in the first initial time window.

19. The system of claim 13, wherein:
the at least two electrodes comprise a first pair of electrodes and a second pair of electrodes;
the pulse generator circuitry is operatively coupled with the first pair of electrodes and the control circuitry is programmed to cause the pulse generator circuitry to generate the first electrical pulse across the first pair of electrodes when the first pair of electrodes is in electrical communication with the at least a portion of the liquid-containing sample; and the signal detection circuitry is operatively coupled with the second pair of electrodes and the control circuitry is programmed to cause the signal detection circuitry:

(i) to detect a first initial electrical response of the at least a portion of the liquid-containing sample due to application of the first electrical pulse to generate at least one first initial electrical response signal indicative of electrical response in a first initial time window extending no longer than a time required to attain 95% of a steady state electrical response value after a change in state of the first electrical pulse, and (ii) to detect a second initial electrical response of the at least a portion of the liquid-containing sample due to application of the second electrical pulse to generate at least one second initial electrical response signal indicative of electrical response in a second initial time window extending no longer than the time required to attain 95% of the steady state electrical response value after a change in state of the second electrical pulse.

20. A method for detecting presence of at least one pathogen in a liquid-containing sample, the method comprising:

supplying at least a first portion of the liquid-containing sample to a fluidic channel to cause the at least a first portion of the liquid-containing sample to contact at least two electrodes in electrical communication with the fluidic channel;

applying a first electrical pulse between the at least two electrodes;

detecting a first initial electrical response of the at least a first portion of the liquid-containing sample due to application of the first electrical pulse, to generate at least one first initial electrical response signal that is indicative of electrical response in a first initial time window that extends no longer than a time required to attain 95% of a steady state electrical response value after a change in state of the first electrical pulse;

supplying at least a second portion of the liquid-containing sample to the fluidic channel to cause the at least a second portion of the liquid-containing sample to contact the at least two electrodes;

applying a second electrical pulse between the at least two electrodes;

detecting a second initial electrical response of the at least a second portion of the liquid-containing sample due to application of the second electrical pulse, to generate at least one second initial electrical response signal that is indicative of electrical response in a second initial time window that extends no longer than the time required to attain 95% of the steady state electrical response value after a change in state of the second electrical pulse; and comparing a second electrical response embodying or derived from the at least one second initial electrical response signal to a first electrical response embodying or derived from the at least one first initial electrical response signal.

* * * * *